United States Patent
Dong et al.

(10) Patent No.: US 10,341,439 B2
(45) Date of Patent: Jul. 2, 2019

(54) SEMANTICS SUPPORT AND MANAGEMENT IN M2M SYSTEMS

(71) Applicant: Convida Wireless LLC, Wilmington, DE (US)

(72) Inventors: Lijun Dong, San Diego, CA (US); Dale N. Seed, King of Prussia, PA (US); Guang Lu, Dollard-des-Ormeaux (CA)

(73) Assignee: Convida Wireless, LLC, Wilmington, DE (US)

( * ) Notice: Subject to any disclaimer, the term of this patent is extended or adjusted under 35 U.S.C. 154(b) by 376 days.

(21) Appl. No.: 14/270,955

(22) Filed: May 6, 2014

(65) Prior Publication Data

US 2014/0330929 A1    Nov. 6, 2014

Related U.S. Application Data

(60) Provisional application No. 61/819,877, filed on May 6, 2013.

(51) Int. Cl.
*G06F 15/167* (2006.01)
*H04L 29/08* (2006.01)
(Continued)

(52) U.S. Cl.
CPC ............ *H04L 67/12* (2013.01); *A61B 5/0022* (2013.01); *A61B 5/0024* (2013.01);
(Continued)

(58) Field of Classification Search
CPC ............ G06F 17/241; G06F 17/30575; G06F 17/2785; G06F 17/2247; G06F 17/227; G06F 19/3418; A61B 5/0022; A61B 5/0024; G16H 50/70; H04L 67/02; H04L 67/12; H04L 67/16; H04W 4/70; H04W 4/08; H04W 4/38; H04W 84/18
See application file for complete search history.

(56) References Cited

U.S. PATENT DOCUMENTS 6,868,447 B1    3/2005  Slaughter et al.
9,052,831 B1 *  6/2015  Stefani .................. G06F 3/0644
(Continued)

FOREIGN PATENT DOCUMENTS

CN      101370030 A     2/2009
JP      2000-156680 A   6/2000
(Continued)

OTHER PUBLICATIONS

"Machine to Machine Communications (M2M); Interworking between the M2M Architecture and M2M Area Network technologies"; ETSI TR 102966 V01.1; European Telecommunications Standards Institute (ETSI); Sep. 2011; 19 pages.
(Continued)

*Primary Examiner* — Ruolei Zong
(74) *Attorney, Agent, or Firm* — BakerHostetler

(57) ABSTRACT

Semantics nodes provide semantics support in machine-to-machine (M2M) systems. In an embodiment, a semantics node may manage semantics related resources capable of being discovered, retrieved, or validated by other devices. In another embodiment, the semantics node may be discovered by other nodes, and semantics related resources may be discovered with subscription mechanisms.

19 Claims, 31 Drawing Sheets

(51) Int. Cl.
*A61B 5/00* (2006.01)
*G06F 19/00* (2018.01)
*H04W 4/38* (2018.01)
*H04W 4/70* (2018.01)
*H04W 4/08* (2009.01)
*H04W 84/18* (2009.01)
*G16H 50/70* (2018.01)

(52) U.S. Cl.
CPC .......... *G06F 19/3418* (2013.01); *H04L 67/16* (2013.01); *H04W 4/38* (2018.02); *H04W 4/70* (2018.02); *G16H 50/70* (2018.01); *H04W 4/08* (2013.01); *H04W 84/18* (2013.01)

(56) References Cited

U.S. PATENT DOCUMENTS

| | | | |
|---|---|---|---|
| 2006/0149709 A1* | 7/2006 | Krakirian | G06F 17/30864 |
| 2007/0179995 A1* | 8/2007 | Prahlad | G06F 17/30528 |
| 2008/0089299 A1* | 4/2008 | Lindsley | H04L 67/104 |
| | | | 370/338 |
| 2008/0313332 A1* | 12/2008 | Wang | H04L 12/4633 |
| | | | 709/226 |
| 2009/0164387 A1* | 6/2009 | Armstrong | G06F 17/241 |
| | | | 705/36 R |
| 2010/0070603 A1* | 3/2010 | Moss | H04L 67/2842 |
| | | | 709/207 |
| 2010/0228693 A1* | 9/2010 | Dawson | G06F 17/2705 |
| | | | 706/12 |
| 2010/0235338 A1* | 9/2010 | Gabriel | G06F 17/3053 |
| | | | 707/706 |
| 2010/0332664 A1* | 12/2010 | Yevmenkin | H04L 29/12405 |
| | | | 709/227 |
| 2011/0113132 A1 | 5/2011 | Petersen et al. | |
| 2011/0276802 A1* | 11/2011 | Roberts | H04L 63/0492 |
| | | | 713/171 |
| 2011/0296517 A1* | 12/2011 | Grigoriev | H04L 63/102 |
| | | | 726/12 |
| 2012/0078612 A1* | 3/2012 | Kandekar | G06F 17/2745 |
| | | | 704/9 |
| 2012/0095958 A1* | 4/2012 | Pereira | G06F 17/3002 |
| | | | 707/609 |
| 2012/0133657 A1* | 5/2012 | Ueno | G06Q 10/06 |
| | | | 345/440 |
| 2012/0232897 A1* | 9/2012 | Pettyjohn | G06Q 30/0603 |
| | | | 704/235 |
| 2012/0254848 A1 | 10/2012 | Robertson et al. | |
| 2013/0013793 A1* | 1/2013 | Sanchez Herrero | H04W 8/04 |
| | | | 709/227 |
| 2013/0016657 A1* | 1/2013 | Muhanna | H04W 4/005 |
| | | | 370/328 |
| 2013/0159451 A1* | 6/2013 | Luciw | H04L 67/2842 |
| | | | 709/213 |
| 2013/0203394 A1* | 8/2013 | Dong | H04W 4/005 |
| | | | 455/414.1 |
| 2013/0238755 A1* | 9/2013 | Woerndle | H04L 67/02 |
| | | | 709/217 |
| 2013/0262576 A1* | 10/2013 | Foti | H04W 4/005 |
| | | | 709/204 |
| 2013/0346398 A1* | 12/2013 | L'Archeveque | G06F 17/30941 |
| | | | 707/722 |
| 2013/0346704 A1* | 12/2013 | Burger | G06F 17/30902 |
| | | | 711/137 |
| 2014/0080528 A1* | 3/2014 | Lim | H04W 48/18 |
| | | | 455/500 |
| 2014/0214535 A1* | 7/2014 | Kee | G06Q 30/0275 |
| | | | 705/14.53 |
| 2014/0258373 A1* | 9/2014 | Lerman | H04L 67/02 |
| | | | 709/203 |
| 2014/0274084 A1* | 9/2014 | Ross | H04L 67/2842 |
| | | | 455/450 |
| 2015/0089061 A1* | 3/2015 | Li | H04L 61/1511 |
| | | | 709/226 |
| 2015/0339146 A1* | 11/2015 | Ponsford | G06F 9/45533 |
| | | | 718/1 |

FOREIGN PATENT DOCUMENTS

| | | |
|---|---|---|
| JP | 2001-290724 | 10/2001 |
| JP | 2004-501427 | 1/2004 |
| JP | 2005-109539 | 4/2005 |
| JP | 2007-080104 A | 3/2007 |
| JP | 2011-526119 | 9/2011 |
| WO | 2007/113164 A1 | 10/2007 |
| WO | 2012/068465 A1 | 5/2012 |
| WO | WO 2012-119246 A1 | 9/2012 |
| WO | WO 2014-182706 | 11/2014 |

OTHER PUBLICATIONS

"Machine to Machine Communications (M2M); Study on Semantic Support for M2M Data"; ETSI TR 101584 V0.5.0; European Telecommunications Standards Institute (ETSI); Dec. 2012; 36 pages.
Machine to Machine Communications (M2M); mIa, dIa and mId interfaces; TS 102921 v1.1.1; European Telecommunications Standards Institute (ETSI); Feb. 2012, 538 pages.
Machine to Machine Communications (M2M); Functional Architecture; TS 102 690 V1.1.1; European Telecommunications Standards Institute (ETSI); Oct. 2011, 280 pages.
International Application No. PCT/US2014/036980: International Search Report and Written Opinion dated Oct. 29, 2014, 10 pages.
Kim et al.; "Seamless Integration of Heterogeneous Devices and Access Control in Smart Homes"; 2012 8th Int'l Conference of Intelligent Environments; Jun. 2012; p. 206-213.
W3C; "Resource Description Framework (RDF): Concepts and Abstract Syntax", Feb. 10, 2004, 21 pages.
W3C; "RDF Vocabulary Description Language 1.0 RDF Schema", Feb. 10, 2004, 12 pages.
Chama et al, "Architecture for Networking Electrical Household Appliances" Universal Plug and Play, Second Volume, Interface issued Jul. 2003, Shuppan K.K., Jul. 1, 2003, 29(7), 164-176.
Japanese Application No. 2016-513017: Notice of Reasons for Rejection dated Jan. 5, 2017, 4 pages.
Korean Patent Application No. 10-2015-7034688: Notice of Allowance dated Aug. 23, 2017, 3 pages (Translation is not available, prior art listed on p. 1).
KR Patent Application No. 10-2015-734688: Office Action dated May 17, 2017, 5 pages, (No Translation available).

* cited by examiner

280

Find some of the existing data of the same application share the same semantics association
281

Classify the data in the same application sharing the same semantics into groups
282

Associate each group with the appropriate semantics
283

Put newly received data from the same application into the group that shares the same semantics
284

FIG. 12

SEMANTICS SUPPORT AND MANAGEMENT IN M2M SYSTEMS

CROSS REFERENCE TO RELATED APPLICATIONS

This application claims benefit under 35 U.S.C. § 119(e) of Provisional U.S. Patent Application No. 61/819,877, filed May 6, 2013, the content of which is incorporated herein by reference in its entirety.

BACKGROUND

The rapid increase in the number of network-enabled devices and sensors deployed in physical environments is changing communication networks. It is predicted that within the next decade billions of devices will generate a myriad of real world data for many applications and services by service providers in a variety of areas such as smart grids, smart homes, e-health, automotive, transport, logistics, and environmental monitoring. The related technologies and solutions that enable integration of real world data and services into the current information networking technologies are often described under the umbrella terms of the Internet of things (IoT) or machine-to-machine (M2M) communications. Because of the large amount of data created by devices there is a need for an efficient way to identify and query this data.

FIG. 1 illustrates an example patient monitoring application that may be provided by a patient's hospital or rehabilitation center using compact biomedical wireless sensor motes that use an actuator as an aggregation point. The actuator transmits data to the network. These small wearable resource constrained devices are examples of M2M devices that may be deployed on a patient to continuously monitor vital signs such as blood pressure and flow, core temperature, oxygen saturation, motion, heart rate, hearing, and vision, among other things. Various kinds of M2M data collected by the M2M devices may be used by the patient's doctor, personal trainer (e.g. from 24 hour fitness), and/or an ambulance service, as depicted in FIG. 1. In order to enable the doctor, personal trainer, and the ambulance service to use the data generated from those M2M device, the semantics of those resources need to be available too. The semantics provide a descriptive definition of the data such that the format and structure of the data can be understood (i.e., the semantics provide meaning for the data).

However, current M2M systems such as the ETSI M2M Architecture described in Draft ETSI TS 102 690 and TS 102 921, do not define mechanisms to support semantics (e.g., data stored within ETSI M2M defined container resources do not have any semantic information that can be stored along with it). As a result, devices and applications need to agree beforehand on a common definition of the exchanged containers as well as on the contained data. This makes re-use of M2M data across different applications difficult in current M2M systems The semantics concept is commonly known in the area of Semantics Web, which is a collaborative movement led by the international standards body known as the World Wide Web Consortium (W3C). The standard promotes common data formats on the World Wide Web. By encouraging the inclusion of semantic content in web pages, the Semantic Web aims at converting the current web dominated by unstructured and semi-structured documents into a "web of data." The Semantic Web stack builds on the W3C's Resource Description Framework (RDF).

FIG. 2 is a diagram illustrating a communication system 120 that implements the ETSI M2M architecture defined by ETSI in its TS 102 690. Note that this diagram is used to assist in understanding of the disclosure and is simplified to facilitate description of the subject matter disclosed herein. As shown in FIG. 2, the system 120 may comprise a plurality of network domains, such as network domain 122, network domain 130, network domain 135, and network domain 138. Each network domain may include a network service capability layer (NSCL), such as NSCL 126, NSCL 131, NSCL 136, and NSCL 139. Each NSCL may interface with a respective network application, such as network application 127 and network application 132 in network domain 122 and network domain 130, respectively.

As further shown, a network domain, such as network domain 122, may further comprise one or more devices, such as device 145 (which for example may be one of the M2M devices used in the patient monitoring application of FIG. 1), and one or more gateways, such as gateway 140. In 3GPP parlance, devices and gateways are examples of UEs. As shown, the device 145 may be running a device service capability layer (DSCL) 146 which communicates with the NSCL 126 over the mId reference point defined by the architecture. A device application (DA) 147 may also be running on the device 145, and it may communicate with the DSCL 146 over a dIa reference point. Similarly, the gateway 140 may implement a gateway service capability layer (GSCL) 141 that communicates with the NSCL 126 over the mId reference point. A gateway application (GA) 142 running on the gateway 140 may communicate with the GSCL 141 via the dIa reference point. In general, dIa reference points allow device and gateway applications to communicate with their respective local service capabilities (i.e., service capabilities available at a DSCL or a GSCL, respectively). The mId reference point allows an M2M SCL residing in an M2M Device (e.g., DSCL 146) or an M2M Gateway (e.g., GSCL 141) to communicate with the M2M service capabilities in the network domain (e.g., NSCL 126) and vice versa.

Still referring to FIG. 2, in greater detail, NSCL 126 may be in domain 122 and be configured with network application (NA) 127 on an M2M server platform 125. NA 127 and NSCL 126 may communicate via reference point mIa 128. The mIa reference points may allow an NA to access the M2M service capabilities available from an NSCL in an M2M domain.

Typically, the device 145, gateway 140, and M2M server platform 125 comprise computing devices, such as the devices illustrated in FIG. 26C and FIG. 26D and described below. The NSCL, DSCL, GSCL, NA, GA, and DA entities typically are logical entities that are implemented in the form of software, executing on the underlying device or platform, to perform their respective functions in the system 120.

As further shown in FIG. 2, NSCL 131 may be in domain 130 with NA 132. NA 132 and NSCL 131 may communicate via mIa reference point 133. There could also be an NSCL 136 in network domain 135, and NSCL 139 in network domain 138 mIm reference point 123 may be an inter-domain reference point that allows M2M network nodes in different network domains, such as NSCL 126 in network domain 122, NSCL 131 in network domain 130, NSCL 136 in network domain 135, or NSCL 139 in network domain 138, to communicate with one another. For simplicity herein, the term "M2M server" may be used to indicate a service capability server (SCS), NSCL, application server, NA, or an MTC server. In addition, the term user equipment (UE), as discussed herein, may apply to a GA, GSCL, DA, or DSCL. A UE, as discussed herein, may be considered a mobile station, a fixed or mobile subscriber unit, a pager, a cellular telephone, a personal digital assistant (PDA), a smartphone, a laptop, a netbook, a personal computer, a wireless sensor or actuator, consumer electronics, and the like. A machine-to-machine services capabilities layer entity as discussed herein may include an M2M server or a UE.

As further background, the Resource Description Framework (RDF) described at http://www.w3.org/TR/rdf-concepts/ is a framework for representing information in the Web. RDF is essentially a data-model. Its basic building block is a resource-property-value triple, called a statement. RDF has been given a syntax in XML.

RDF includes the concepts of resources, properties, values, and statements. A resource may be thought of as an object or a "thing." Resources may be authors, books, publishers, places, people, hotels, rooms, search queries, and the like. The resource has a universal resource identifier (URI). A URI may be a unified resource locator (URL), Web address, or some other kind of unique identifier. The identifier does not necessarily enable access to a resource. URI schemes have been defined for web-locations, but also for such diverse objects as telephone numbers, ISBN numbers, and geographic locations. Properties may be considered special kinds of resources, and describe relations between resources, for example "written by," "age," "title," and the like. Properties in RDF are also identified by URIs and by URLs.

Values may be resources or literals. Literals are atomic values (strings). For example, a resource having a property of "age" can have a literal value of "20." Statements assert the properties of resources. A statement is a resource-property-value triple, consisting of a resource, a property, and a value. The underlying structure of an expression in RDF is a collection of triples, each consisting of a resource, a property, and a value. Each triple represents a statement of a relationship between the things denoted by the nodes that it links.

RDF is domain-independent, in which no assumptions about a particular domain of use are made. It is up to the users to define their own terminology in a schema language called RDF Schema (RDFS). RDFS defines the vocabulary used in RDF data models. In RDFS we can define the vocabulary, specify which properties apply to which kinds of objects and what values they can take, and describe the relationships between objects.

The core classes defined by W3C are
rdfs:Resource, the class of all resources
rdfs:Class, the class of all classes. The group of individuals that belongs to a class shares the same properties.
rdfs:Literal, the class of all literals (strings)
rdf:Property, the class of all properties.
rdf:Statement, the class of all reified statements
The core properties defined by W3C are
rdf:type, which relates a resource to its class. The resource is declared to be an instance of that class.
rdfs:subClassOf, which relates a class to one of its superclasses. Instances of a class are instances of its superclass.
rdfs:subPropertyOf, relates a property to one of its superproperties.
rdfs:domain, which specifies the domain of a property P, or specified subjects of the property in the triple.
rdfs:range, which specifies the range of a property P. The class of those resources that may appear as values in a triple with predicate P.

With the foregoing discussion of M2M systems and the RDF and RDFS as background, the present application is directed to systems and method for semantic support and management in M2M systems.

SUMMARY

In current M2M systems, M2M service layers lack semantic awareness capabilities and hence data flowing through or stored within M2M service layers is treated as opaque information. To address this shortcoming, proposed herein is the concept of a semantics node. A semantics node is a logical entity that may be hosted on a standalone server in the network or hosted on an existing entity within the network, such as an M2M gateway, device, server, or the like. A semantics node stores and manages semantics related resources. In one embodiment, semantics related resources may have one of three types: class, relationship, and term. A semantics related resource comprises information that can be used to describe the semantics information of a thing, such as the meaning of data generated by an M2M device or application or the M2M device or application itself. This categorization provides compatibility with current techniques of the semantics web and enables an M2M system to leverage existing semantics related resources.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE DRAWINGS

A more detailed understanding may be had from the following description, given by way of example in conjunction with the accompanying drawings wherein:

FIG. 12 illustrates a flow diagram of grouping of resources with the same semantics;

DETAILED DESCRIPTION OF ILLUSTRATIVE EMBODIMENTS

In current M2M systems, M2M applications (hosted on devices as well as backend network servers) need to agree beforehand on a common definition of exchanged data. This is primarily due to a lack of semantic aware M2M service layers that are able to parse, interpret, or process M2M data on behalf of applications. In current M2M systems, M2M service layers lack semantic awareness capabilities and hence data flowing through or stored within M2M service layers is treated as opaque information.

This lack of semantic awareness prevents M2M service layers from offering services which allow data produced by M2M applications to be effectively abstracted or virtualized by the M2M service layer such that it can be discovered, accessed, interpreted, and shared by different applications even if they do not have any prior knowledge of the application from which the data originated. As a result, the physical entities that are sensed and acted upon (e.g. appliances, people, cars, rooms of a building, etc.) may not be effectively virtualized/abstracted by M2M service layers and the physical entities are treated as generic entities, intrinsic to the environment, and not tied to a specific M2M application.

In order to overcome this limitation, the data transmitted in M2M systems needs to be associated and integrated with semantic information, such that semantic aware M2M service layers can have the same knowledge of the data as M2M applications. In doing so, M2M service layers can better facilitate the sharing of data across applications and provide value-added semantic aware services to M2M applications (e.g., data aggregation, data sharing amongst different applications, etc).

Figure 1:
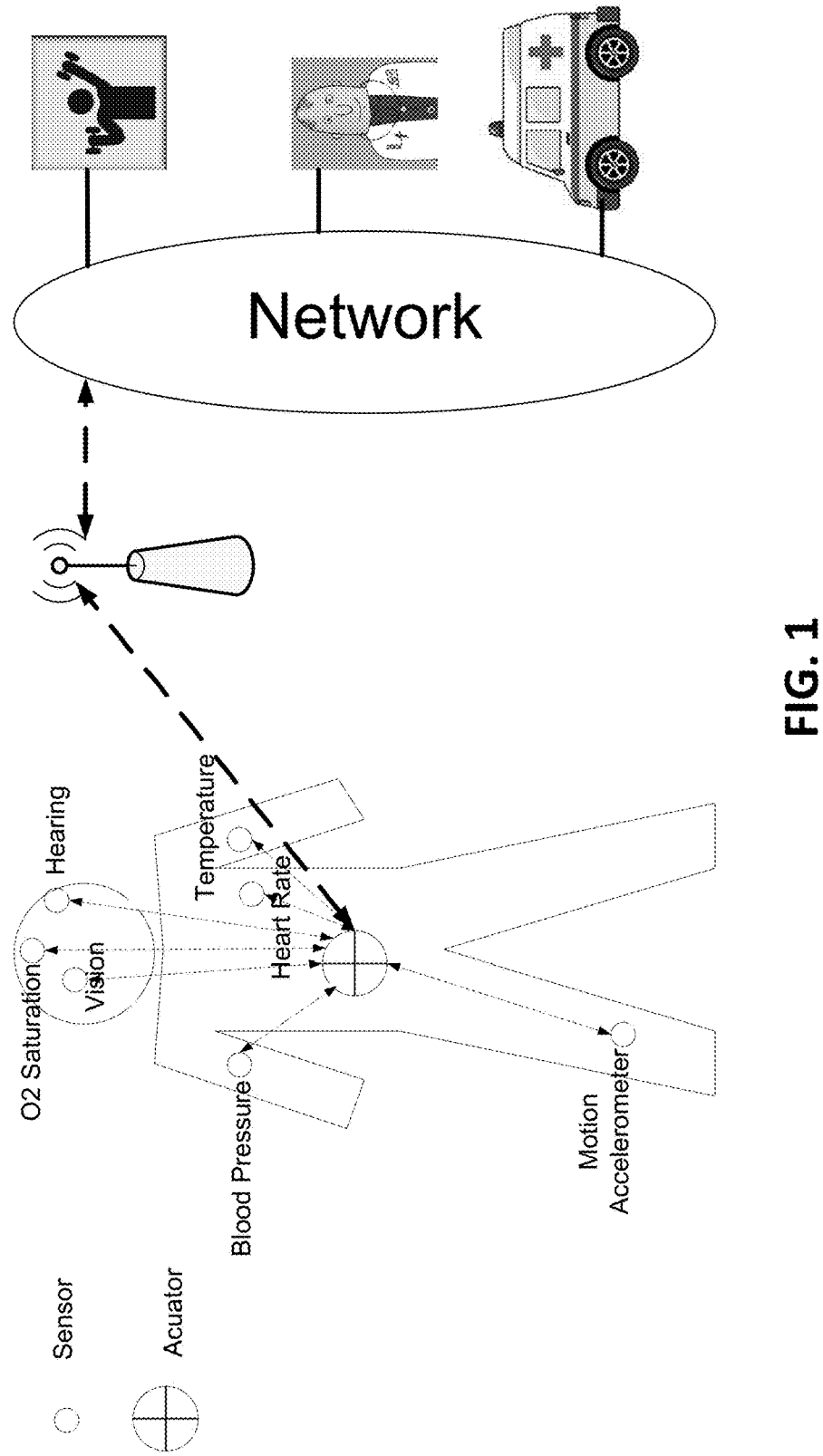
FIG. 1 illustrates a patient monitoring application.
Figure 2:
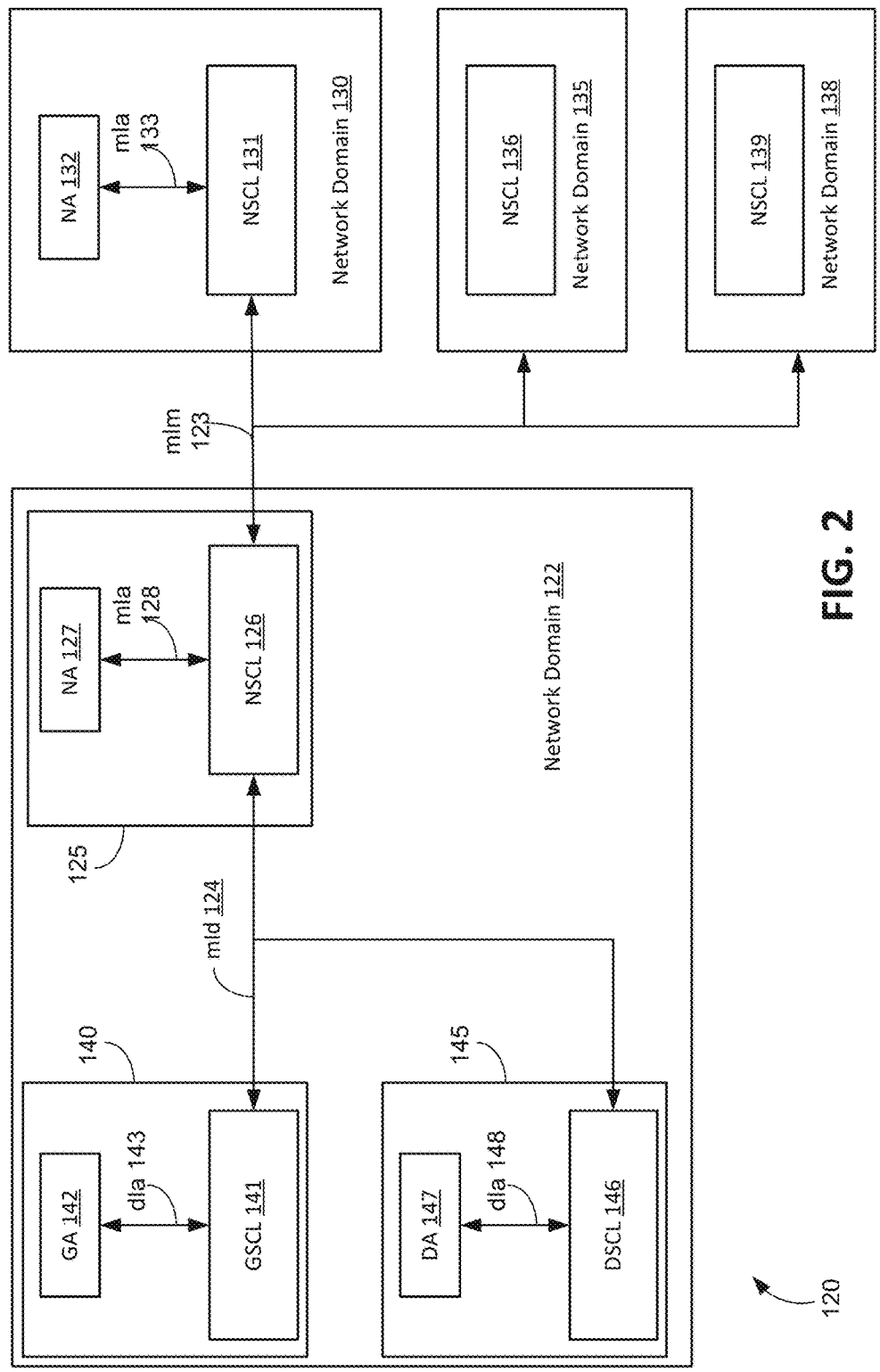
FIG. 2 illustrates an ETSI M2M architecture.

For example, in the patient monitoring application illustrated in FIG. 1, there could be separate applications hosted on each of the wireless sensor devices that monitor a patient's vital signs (e.g., blood pressure, temperature, oxygen, heart rate, etc). Likewise, there could be separate applications hosted in the network that could make use of this information (e.g., patient's doctor, personal trainer, family members, ambulance paramedics, etc). However, without M2M semantic aware services data from each of the wireless sensor devices, network applications may have difficulty discovering, sharing, and understanding the information from device applications unless the network applications have prior knowledge of the applications hosted on the wireless sensor devices and the type of information they produce (e.g. the location/address, units of the data, context of the data, etc).

The present application aims to provide the following functionalities in an M2M system to support M2M service layer semantic awareness and data abstraction: (i) support for storing semantics information, and/or support for interfaces to servers storing semantics information; (ii) support for mechanisms for creating, retrieving, updating, and deleting semantics information; (iii) support for mechanisms for semantic information updates to local and remote resources; (iv) support for associating/linking semantic information with corresponding resources which may be stored either locally or remotely; and (v) capabilities to publish and discover semantic descriptions.

In order to provide one or more of the functionalities mentioned, the present application discloses the concept of a semantics node. As described herein, a semantics node is a logical entity that may be hosted on a stand-alone computing device (e.g., server) in the network or hosted on an existing entity within the network, such as an M2M gateway, M2M device, M2M server, or the like. A semantics node may be seen as a repository that describes data. For example, a sensor device for blood pressure may want to understand how to describe its data, so it queries a nearby semantics node to find out if there is a blood pressure class already defined. If so, the semantics node responds to the sensor device with the blood pressure class it found locally. If not, the semantics node may query other semantics nodes (e.g., siblings or parents). The use of a semantics node may reduce the need to have end devices store descriptions of data.

A semantics node stores and manages semantics related resources, which are stored on the semantics node. Semantics related resources usually describe other resources, such as, for example, the ETSI M2M resources that are stored under the resource tree, <SCL>, <application>, <container>, <contentInstance>, which need to have semantics related resources associated with them in order to enable an understanding of their semantics. In one embodiment, semantics related resources may have one of three types: class, relationship, and term. This categorization provides compatibility with current techniques of the semantics web and enables an M2M system to leverage existing semantics related resources.

As discussed herein, semantics nodes may be deployed in an M2M system in different levels, such as a M2M area network, a M2M access network, and a M2M core network, such that the different levels form into a hierarchical structure. Semantics nodes in the same level may be distributed and have a sibling relationship. Mechanisms are disclosed with regard to building and maintaining such a hybrid architecture of semantics nodes, which provides the benefits of different levels of abstraction and compatibility to an existing network hierarchy.

Functions, reference points, messages, and procedures for the semantics node are also disclosed. In various embodiments, the following functionalities may be enabled on a semantic node: (i) semantics related resources managed by the semantics node are capable of being discovered, retrieved, and validated; (ii) semantics nodes may be discovered by other nodes and semantics related resources may also be discovered with subscription mechanisms; (iii) semantics related resources may be linked and associated with resources in the M2M system such that the semantics related resources are provided with semantics information and universally understood; (iv) semantics related resources may be pushed to other semantics nodes in the hierarchy for the purpose of efficient discovery and easy access; (v) semantics related resource association and linking may be optimized based on the semantics similarity and grouping of semantics related resources being described; and (vi) semantics related resources may be moved from one semantics node to another semantics node, along with the data movement.

In one embodiment described hereinafter, the semantics node is implemented in the service capability layers (xSCLs) of the ETSI M2M/oneM2M architecture. In another embodiment, the semantics node is implemented in a service capability server (SCS) of the 3GPP Machine Type Communication (MTC) architecture.

I. M2M Architecture with Semantics Nodes

Figure 3:
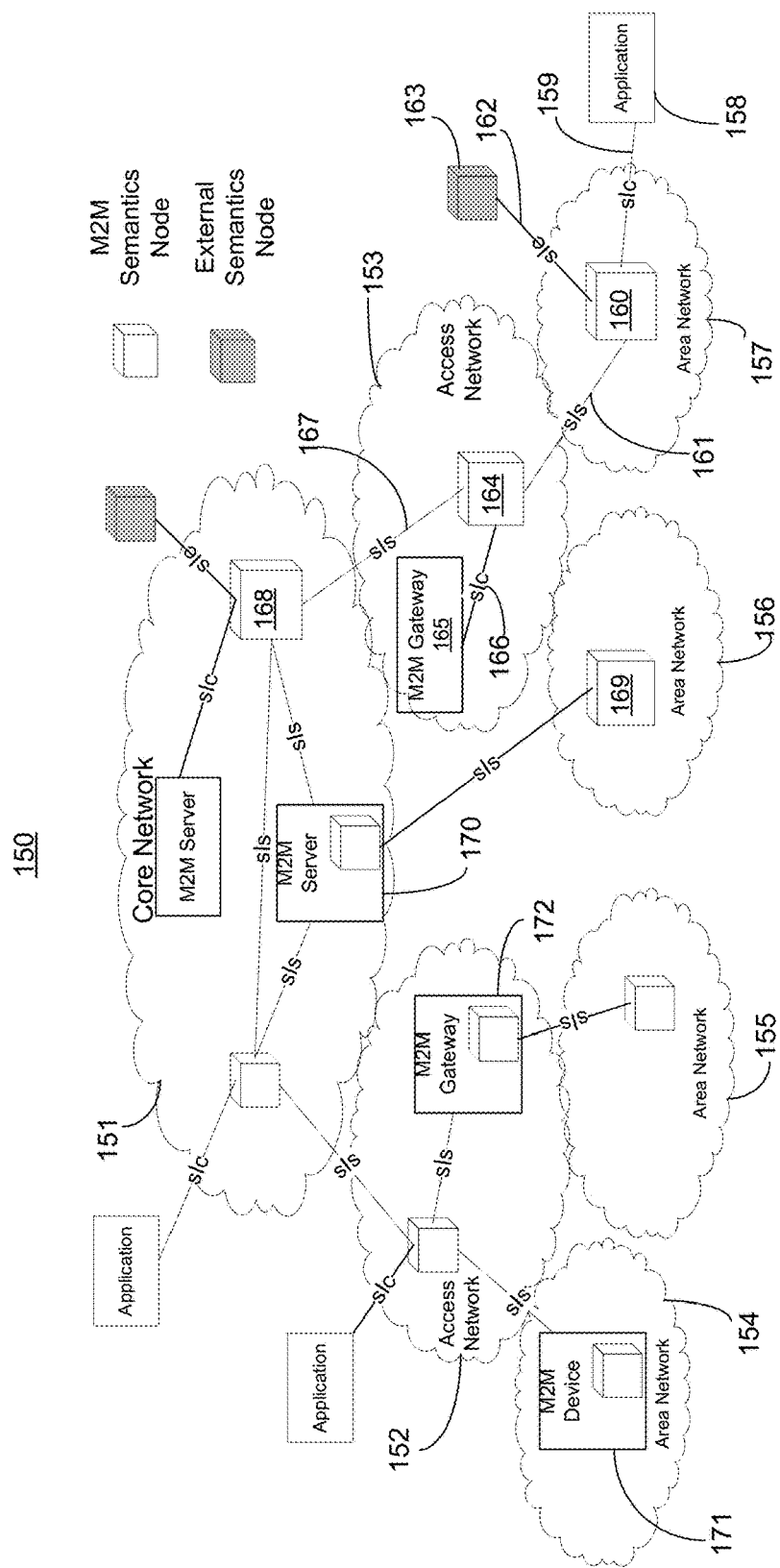
FIG. 3 illustrates a M2M Architecture with semantics nodes.

One embodiment of a M2M system that includes semantics nodes is illustrated in FIG. 3. As shown in M2M system 150 the semantics nodes are deployed at three levels. There may be an area level, which may include networks, such as area network 154, area network 155, area network 156, and area network 157. There may be an access level, which may include networks, such as access network 152 and access network 153. And there may be a core level, which includes a network, such as core network 151.

As shown in system 150, application 158 may be communicatively connected with M2M semantics node 160 located in area network 157 via reference point sIc 159. The sIc reference point is generally used by applications, other non-semantics node entities in the area network, access network, and core network entities to talk to a semantics node. M2M semantics node 160 is communicatively connected with external semantics node 163 via reference point sIe 162. The semantics nodes in M2M systems may interface with external semantics nodes via the sIe reference point. The external semantics nodes may manage other existing semantics related resources such as those defined by RDFS for the semantics web. M2M semantics node 160 is also communicatively connected with M2M semantics node 164 located in access network 153 via sIs reference point 161. M2M semantics node 164 is communicatively connected with M2M gateway 165 via sIc reference point 166 and communicatively connected with M2M semantics node 168 located in core network 151 via reference point sIs. In this embodiment, the M2M Gateway 165 itself is not a semantics node, but in other embodiments, the M2M Gateway 165 could incorporate the functionality of semantics node.

Semantics node(s) may be deployed at the area level for the purpose of offloading, load balancing, easy access, etc. At the area level, it is possible that there is no semantics node deployed if all the devices in the local area network communicate with a semantics node in the attached access or core networks. A semantics node at the area level may have a corresponding parent semantics node at the access level (e.g., M2M semantics node 160 connected with M2M semantics node 164) or at the core level (e.g., M2M semantics node 169 connected with M2M server 170 that includes a semantics node). Semantics nodes talk to each other through the sIs reference point. The details of the reference points are defined further hereinafter. A semantics node at the access level may also have a parent at the core level, which it communicates with over the sIs reference point. Likewise, a semantics node at the access level may have children semantics nodes at the area level, which it communicates with via the sIs reference point. Semantics nodes at the core level may also have children semantics nodes at the access or area level.

In addition to the parent-child relationships illustrated in FIG. 3, the semantics node also supports a notion of siblings at any of the semantics node levels (e.g., access, area, or core). Sibling semantics nodes are nodes at the same level in the hierarchy and can be used to distribute the load of the semantics node. For example, in core network 151, M2M semantics node 168 is connected with M2M server 170 that includes a semantics node. From a vertical perspective, if there is an established hierarchy of more than one semantics node, then the nodes can talk to each other and share semantics information, via notification, broadcast, discovery, etc. over the sIs reference point.

For a constrained device, due to the limit of capacity, the semantics can be a code referring to a specific semantic or a link pointing to the semantics stored in a remote semantics node. Such semantic information may be provided by the application that created the data or by the service layer.

At the access level, there might be one or more semantics nodes deployed in one access network. If so, the siblings may communicate with each other for semantics information notification, broadcast and discovery through the sIs reference point. A semantics node at the access level may also have a parent at the core level which it communicates with over the sIs reference point. Likewise, a semantics node at the access level may have children semantic nodes at the area level which it communicates with via the sIs reference point.

At the core level, there might be one or more semantics nodes deployed in the core network. These nodes may be siblings and communicate with each other over sIs reference point for sharing semantics information using notification, broadcast and discovery. Semantics nodes at the core level may also have children semantic nodes at the access or area level. Applications, other non-semantics-node entities in the area network, access network and core network talk to a semantics node via the sIc reference point.

As mentioned above, a semantics node may be a standalone physical node in a network (e.g., standalone M2M semantics node 160) or it can be a logical entity hosted on another physical node in the network, such as an M2M device 171, M2M gateway 172, or M2M server 170, as shown in system 150 of FIG. 3. In the other words, an M2M device, M2M gateway, and M2M server can support semantics node functionalities.

A feature of the multi-layer semantics node hierarchy illustrated in FIG. 3 is that it can provide different levels of abstraction. A semantics node may only be in charge of managing the semantics related resources in a localized area, such as in a M2M area network, such that the area network specific semantics related resources may be found locally. Any semantics related resources that are not typical in the localized area can be stored and found in higher-level parent or parallel sibling semantics nodes. Another feature is that the semantics related resources may have a hierarchy themselves due to the Internet hierarchy, the location hierarchy, etc. As a result, the multiple layers of semantics are coherent with the existing network architecture. In addition, semantics nodes may be distributed in each level, which prevents a single failure point if a centralized semantics node is deployed only in the core network.

II. Semantics Node Architecture

More details regarding the architecture of a semantics node will now be discussed. As mentioned, a semantics node stores and manages semantics related resources. As defined herein, a semantics related resource comprises information that can be used to describe the semantics information of a thing, such as the meaning of data generated by an M2M device or application or the M2M device or application itself. In one embodiment, semantics related resources may be expressed in extensible markup language (XML) using existing schemas, such as XML Schema Definition (XSD), RDF Schema/Web Ontology Language (RDFS/OWL), or the like. In an embodiment, three types of semantics related resources may be stored in a semantics node—classes, relationships, and terms—each of which is described more fully below. The categorization of semantics related resources in this manner provides compatibility with the current techniques of the semantics web. This compatibility enables an M2M system to leverage existing semantics related resources, such as for example those core classes and core properties defined by W3C. Applications and entities external to the M2M system are able to use the semantics related resources hosted by the semantics node, without incurring any extra overhead due to format conversion or modification necessary to make the semantics compatible.

Classes.

Discussed herein is the concept of classes of objects/things in an M2M domain. In the example health monitoring system of FIG. 1, for example, the classes of objects relevant to the system include patient, doctor, ambulance dispatcher, blood pressure, core temperature, oxygen saturation, motion accelerometer and the like. A class may be identified by a uniform resource identifier (URI) or a uniform resource locator (URL). A class contains field descriptions that contain information defining the class. For example, a temperatureReading class that represents temperature data as an integer in units of Celsius and can be used, for example, to provide those semantics to data generated by a temperature sensor may be defined in XML with the schema of XSD as follows:

```
<simpleType name="temperatureReading">
    <restriction>
        description ="temperature in Celsius" unit="Celsius" base="integer"
    </restriction>
</simpleType>
```

Here, the class contains the fields "description," "unit," and "base," and the information in those fields is "temperature in Celsius," "Celsius," and "integer," respectfully. As another example, a BloodPressure class may contain two fields, one for systolic pressure and another for diastolic pressure. The class description for this BloodPressure class would include both fields' descriptions and may be expressed using XML/XSD as follows:

```
<complexType name="BloodPressure">
    <sequence>
        <element name="systolicINmmHG" type="integer"/>
        <element name="diastolicINmmHG" type="integer"/>
    </sequence>
</complexType>
```

Again, however, it is understood that classes (and the other types of semantic related resources—relationships and terms) are not limited to expression using XML/XSD but rather may be expressed in any of a variety of suitable description languages, including, for example, RDFS/OWL and the like. Classes may also be related to each other. For example, "blood pressure" may be a subclass of "vitals", or equivalently, "vitals" may be a superclass of "blood pressure." The subclass/superclass relationships define a hierarchy of classes. In general, A is a subclass of B if every instance of A is also an instance of B. A class may have multiple super classes.

Relationships.

Relationships are a special kind of semantics related resource. Relationships describe relations between semantics related resources, for example "created by," "lifetime," "subscribed by," and so on. A relationship can also be identified by a URI/URL, which gives a global and unique naming scheme to relationships of the M2M domain. Classes and inheritance are known in other fields of computing, for example in object-oriented programming. But while there are similarities, differences exist too. In object-oriented programming, an object class defines the relationships or properties that apply to it. To add new relationships or properties to a class means to modify the class. However, here, relationships are defined globally, that is, they are not encapsulated as attributes in class definitions. A new relationship may be defined that applies to an existing class without changing the definition of the class itself. Like classes, the relationships can also be related to each other. For example, "energy mode" and "usage mode" are sub-relationships of "mode". If a device has an "energy mode" of electric and a "usage mode" of manual, then it has a "mode" of electric and manual.

Terms.

Terms are concepts that are commonly used in an M2M domain. As defined herein, a term is a value that may be used by many parties to describe the semantics of a resource. The definition of a term may be universally acknowledged in certain domains where it is published. For example, manual, user-directed, and autonomous are each examples of terms that may be used to describe, for example, an appliance's usage mode. In general, the creator of a semantics related resource will determine whether that semantics related resource is a class, relationship, or term. A semantics node will then store the semantics related resources under the categories defined or determined by their creator. For example, in the patient monitoring example of FIG. 1, semantics related resource classes, relationships, and terms may be created by a blood pressure monitor manufacturer, by a doctor, or by another appliance manufacturer. In other examples, semantics related resource classes, resources, and terms may be defined or created by a vertical application.

The semantics of a resource (including data, thing, etc.) can be described by a resource-relationship-value triple, consisting of a resource, a relationship and a value. Values can either be classes, terms, or other resources. The following are some examples, A content instance (resource) hasType (relationship) temperatureReading (class)

An appliance (resource) hasUsageMode (relationship) user-directed (term)

A content instance (resource) generatedBySameApplicationAs (relationship) another content instance (resource)

Figure 4:
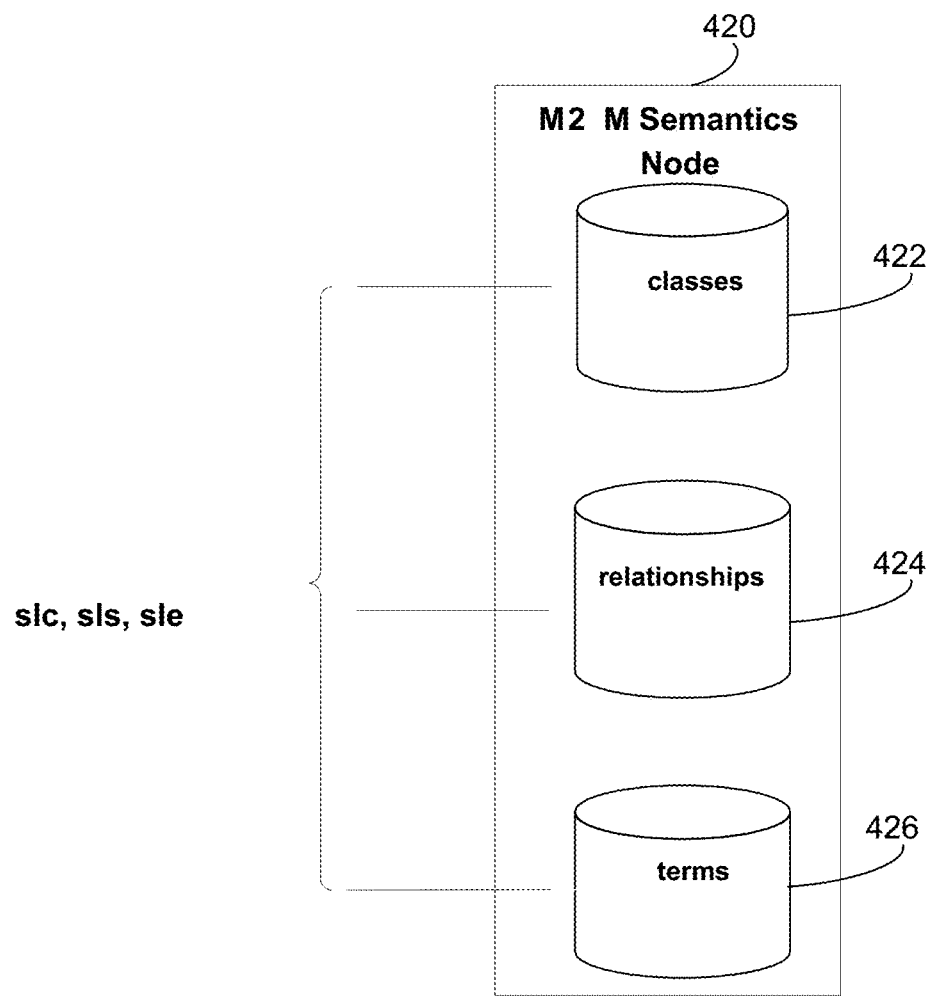
FIG. 4 illustrates a M2M semantics node architecture.

Through the proposed sIc, sIs and sIe reference points, requests to a semantics node's class, relationship and term resources can be made. FIG. 4 is an exemplary illustration of an M2M semantics node's class, relationship and term resources. As illustrated in this example, a semantics node 420 may be configured to store various classes 422, relationships 424 and terms 426 from different applications and domains. Alternatively, the semantics node 420 may be configured to store class, relationship, and term resources for a unique application or domain, such as appliance semantics, vehicle semantics, health care application semantics, or the like.

III. M2M Semantics Node Functions and Reference Points

In this section, further details concerning the functions and reference points of a semantics node are provided. In one embodiment, a semantics node may perform the following functions: authenticating other semantics nodes including authenticating lower level children or parallel sibling semantics nodes in a semantic node hierarchy to allow them to register and make requests for a semantic node's resources; authenticating applications, devices, and/or users to allow them to publish, create, delete, update, and retrieve semantics related classes, relationships and terms resources; storing and managing semantics related classes, relationships and terms resources; providing support for discovery of semantics related resources; and providing support for semantics nodes to communicate with one another (between parent-child, siblings) in order to collaborate on discovery queries and share semantics related resource information.

A semantics node may communicate with other entities in the network via one or more reference points or interfaces. In one embodiment, three reference points are defined—an sIs reference point, an sIc reference point, and sIe reference point. The sIs reference point is used for communication between semantics nodes. The sIs reference point may also be used by a semantics node to register to another semantics node to form parent-child or sibling relationships, to discover other semantics nodes, to notify others about its status (e.g., online, offline, overloaded, etc.), to trigger another semantics node to perform a particular operation (e.g., de-registration, registration), to publish, create, delete, update, and retrieve semantics related resources in another semantics node. In addition, a semantics node may use the sIs reference point to subscribe to semantics related resources in another semantics node and to receive corresponding notifications, to discover semantics related resources on the siblings and parent semantic nodes in its hierarchy, to move a group of semantics related resources from one semantics node to another semantics node, and to allow the semantics related resources stored in another semantics node to be linked and associated with a resource to provide the semantics to that resource, as described further below in connection with FIG. 20, FIG. 21, and FIG. 22.

In the present embodiment, the sIc reference point may be used by an application or non-semantics node to communicate with a semantics node from various network domains (e.g., area network, access network, or core network). The sIc reference point also allows an application or non-semantics node to publish, create, delete, update, retrieve, subscribe to, or discover semantics related resources in a semantics node and to receive notifications from the semantics node. In addition, the sIc reference point allows the semantics related resources stored in a semantics node to be linked and associated with a resource to provide the semantics to that resource.

The sIe reference point may be used for communication between a semantics node that is part of an existing hierarchy of nodes in an M2M system and an external semantics node. An external semantics node stores semantics-related resources outside of the M2M domain. One example of an external semantics node may be a server that stores the semantics-related resources for Semantic Sensor Network Ontology that is defined by the W2C Semantic Sensor Network Incubator Group, as described at http://www.w3.org/2005/Incubator/ssn. The sIe reference point allows a semantics node to retrieve, discover, and subscribe to semantics related resources in an external semantics node and vice versa. Also via the sIe reference point, external semantics nodes may discover semantics nodes in the M2M system and receive notifications.

One embodiment of the messages associated with the sIs, sIe, and sIc reference points, which effectively define those reference points, are set forth below in Table 1.

Table 1 lists semantics node related messages, there corresponding meanings, and reference points used.

TABLE 1

Semantics Node Messages

| Message | Description | Reference Point |
|---|---|---|
| SEMANTICS_NODE_DISCOVERY_REQ/RESP | Discover individual semantics nodes to build the hierarchy of semantics nodes and sibling relationship. | sIs, sIc, sIe |
| SEMANTICS_NODE_REGISTER_REQ/RESP | Register to the upper-level semantics ode to build the parent-child relationship. | sIs |
| SEMANTICS_NODE_DEREGISTER_REQ/RESP | De-register from the upper-level semantics node to release the parent-child relationship. | sIs |

TABLE 1-continued

Semantics Node Messages

| Message | Description | Reference Point |
|---|---|---|
| SEMANTICS_NODE_STATUS_NOTIFY | Notify the status of a semantics node, e.g. online, offline, overloaded, etc. | sIs |
| SEMANTICS_NODE_DE-REGISTER_TRIGGER | Trigger a semantics node to de-register from the current parent, the new candidate parent may be piggybacked. | sIs |
| SEMANTICS_NODE_REGISTER_TRIGGER | Trigger a semantics node to register to another semantics node as parent while the current parent goes offline or proactively releases the parent-child relationship. | sIs |
| SEMANTICS_RELATED_RESOURCE_CREATE_REQ/RESP | Create semantics related resources in types of class, relationship, term in a semantics node | sIs, sIc |
| SEMANTICS_RELATED_RESOURCE_RETRIEVE_REQ/RESP | Retrieve semantics related resources in types of class, relationship, term in a semantics node | sIs, sIc, sIe |
| SEMANTICS_RELATED_RESOURCE_UPDATE_REQ/RESP | Update semantics related resources in types of class, relationship, term in a semantics node | sIs, sIc |
| SEMANTICS_RELATED_RESOURCE_DELETE_REQ/RESP | Delete semantics related resources in types of class, relationship, term in a semantics node | sIs, sIc |
| SEMANTICS_RELATED_RESOURCE_SUBSCRIBE_REQ/RESP | Subscribe to semantics related resources in types of class, relationship, term in a semantics node | sIs, sIc, sIe |
| SEMANTICS_RELATED_RESOURCE_SUBSCRIBE_NOTIFY | Notify the subscribers of the semantics related resource update | sIs, sIc, sIe |
| SEMANTICS_NODE_RESOURCE_SUBSCRIBE_REQ/RESP | Subscribe to a semantics node's stored and managed semantics related resources, with conditions set up. | sIs, sIc, sIe |
| SEMANTICS_NODE_RESOURCE_SUBSCRIBE_NOTIFY | Notify the subscribers of the semantics related resource update from the semantics node. | sIs, sIc, sIe |
| SEMANTICS_RELATED_RESOURCE_MODIFY_REQ/RESP | Modify a semantics related resource to suit the requester's requirement, which may be implemented by UPDATE and CREATE RESTFUL operations. | sIc |
| SEMANTICS_RELATED_RESOURCE_DISCOVERY_REQ | Discover existing semantics related resources in types of class, relationship, term by setting up the search strings (key words) | sIs, sIc, sIe |
| SEMANTICS_RELATED_RESOURCE_DISCOVERY_RESP | Respond to a semantics related resource discovery request by returning the address (e.g. URL/URI) of the matching semantics related resources | sIs, sIc, sIe |
| SEMANTICS_LINKAGE_CREATE_REQ/RESP | Create semantics linking and association between a M2M data/resource and a semantics related resource. | sIs, sIc, sIe |
| SEMANTICS_LINKAGE_UPDATE_REQ/RESP | Update semantics linking and association between a M2M data/resource and a Semantics related resource. | sIs, sIc, sIe |
| SEMANTICS_LINKAGE_RETRIEVE_REQ/RESP | Retrieve semantics linking and association between a M2M data/resource and a semantics related resource. | sIs, sIc, sIe |

TABLE 1-continued

Semantics Node Messages

| Message | Description | Reference Point |
|---|---|---|
| SEMANTICS_LINKAGE_DELETE_REQ/RESP | Delete semantics linking and association between a M2M data/resource and a semantics related resource. | sIs, sIc, sIe |

Protocols such as hypertext transfer protocol (HTTP) or constrained application protocol (CoAP) may be used as an underlying transport protocol for carrying the different types of messages. Examples are presented below of the use of these messages to perform the various semantic node functionalities discussed above

IV. M2M Semantics Node Procedures

A. Build Semantics Node Hierarchy

In this section, additional details are provided regarding how a hierarchy of semantics nodes (hereinafter "semantics node hierarchy") may be built, in accordance with one embodiment. In this embodiment, a semantics node hierarchy is built up by determining the parent-child and sibling relations between the semantics nodes located at the different area, access, and core levels in a network.

Figure 5A:
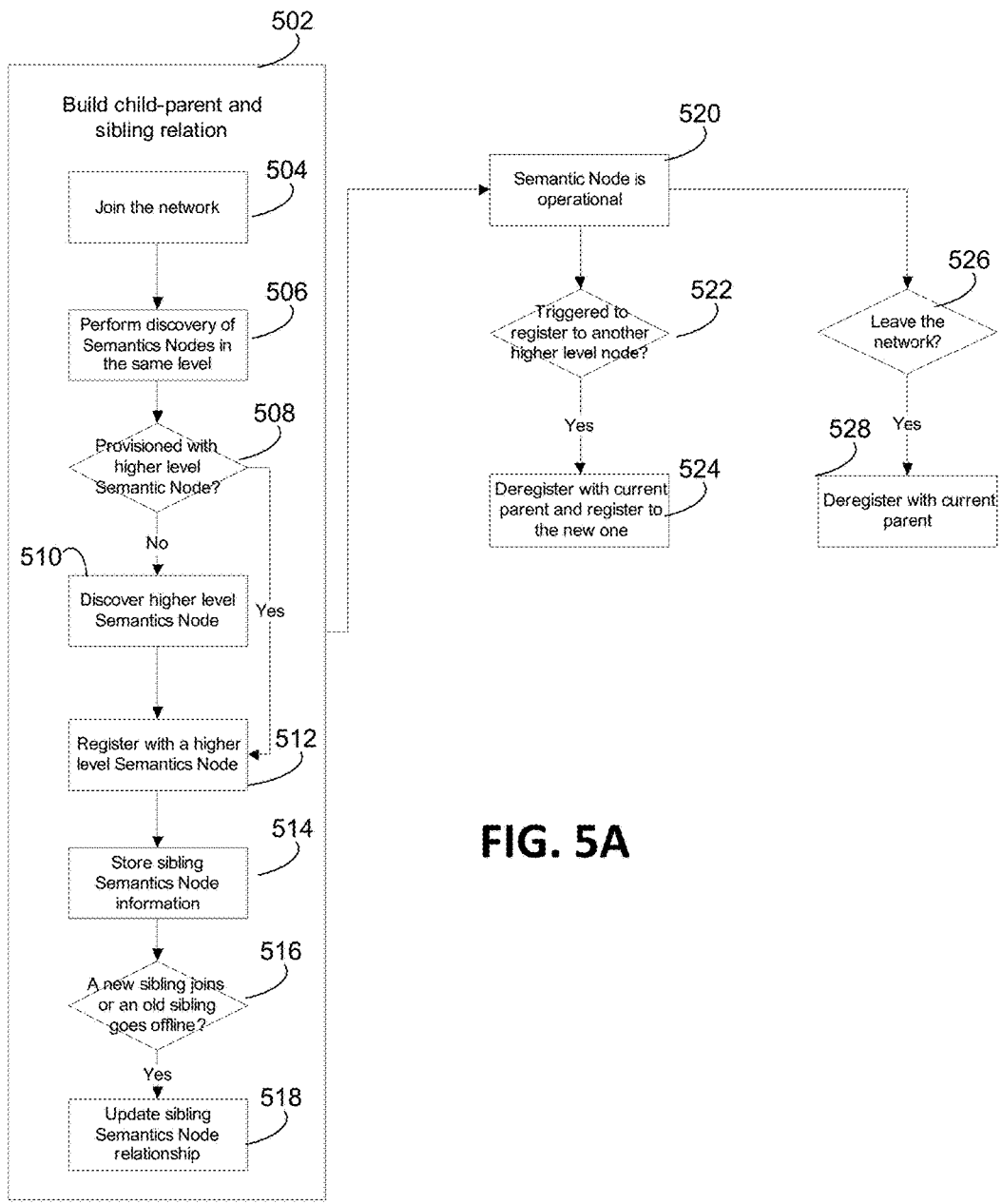
FIG. 5A is a flow diagram illustrating one embodiment of a method for establishing a semantics node hierarchy.

FIG. 5A is a flow diagram illustrating one embodiment of a method for establishing a semantics node hierarchy. When a semantics node joins the network (step 504), i.e. becomes online, it needs to first build the child-parent and sibling relations before it can become an operational Semantic Node in the network. To this end, in step 506, the semantic node may perform discovery of sibling semantics nodes in the same level.

The discovery of sibling semantics nodes may be based on sending out semantics node discovery requests (e.g., multicast, broadcast, anycast) where a discovery request can be issued in an attempt to discover sibling semantics nodes. The request can have a defined hop-limit that limits the flooding of discovery request and response messages, which may congest the network. Alternatively, the discovery can leverage existing discovery mechanisms available within the network, such as domain name system (DNS), DNS service discovery (DNS-SD), service location protocol (SLP), etc, if available. A semantics node may store the returned information of the neighboring sibling semantics nodes, such as IP address or type(s) of semantics information managed. As discussed further below, the sibling semantics node discovery response message may also piggyback the address of a higher-level semantics node discovery server, the address of a parent semantics node of the sibling, or both.

Figure 5B:
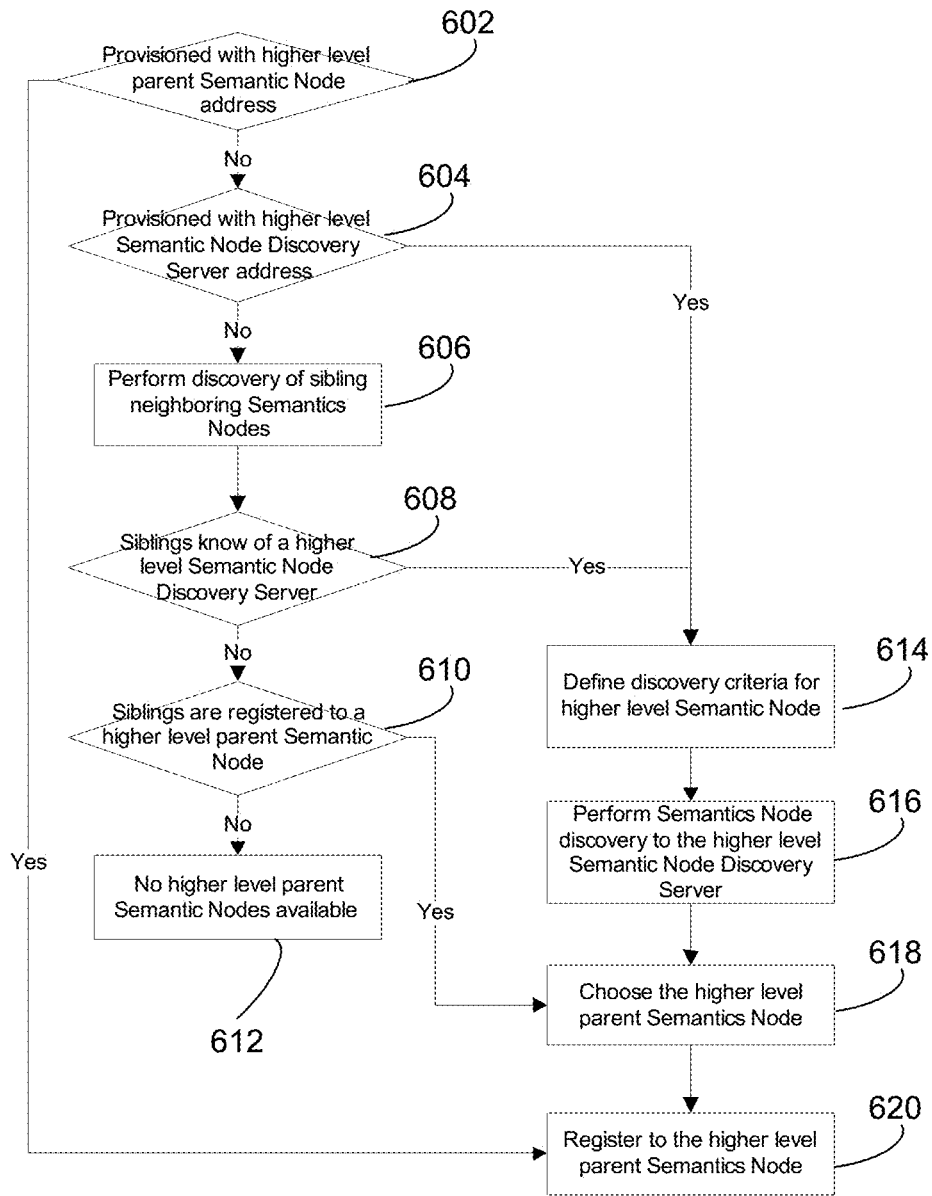
FIG. 5B illustrates steps in FIG. 5A in more detail.

Referring still to FIG. 5A, following discovery of sibling semantic nodes, the semantic node may next attempt to discovery and/or register with higher level semantic nodes in step 508, step 510, and step 512. If the semantics node is provisioned with the higher level node that it needs to register with, it can simply register with this provisioned semantics node and build the parent-child relationship (step 508, step 512). Otherwise, the semantics node needs to discover the existing higher level semantics nodes, and choose one of them to register with (step 510). The choice may be based on a criterion such as nearest in the adjacent upper level, supporting the same type(s) of semantics resources, and the like. FIG. 5B illustrates these step 508, step 510, and step 512 in more detail.

In the present embodiment, at each level, there may be one semantics node discovery server, which accepts a higher-level semantics node discovery request by default. The address of the semantics node discovery server may be well known to the lower level semantics nodes. As shown in FIG. 5B, if the new semantic node is not provisioned with a higher level parent semantic node address (step 602), and if the new semantics node is not provisioned with the semantics node discovery server in the upper level (step 604), it can firstly perform sibling semantics node discovery 606. As part of sibling discovery, the address of the semantics node discovery server may be shared (e.g., piggybacked in the sibling discovery response received from a discovered sibling semantic node) (step 608). On the other hand, it may also explicitly request the siblings' parent semantics node information (address) such that it may choose one as its own parent to which to register (steps 610, 618).

If the new semantics node is provisioned with the upper level semantics node discovery server's address, it can perform the semantics node discovery directly (control passes from step 604 to step 614). Otherwise, it decides whether it wants to choose from the siblings' parent list and whether it wants to retrieve the default semantics node discovery server's address from siblings (steps 608 and 610). If the new semantics node chooses an upper-level semantics node from the siblings' parents (step 618), it may choose not to perform the semantics node discovery further. Otherwise, it decides the criteria of choosing the parent (nearest in hop count, supporting the same type(s) of semantics resources, etc.) (step 614). Based on the criteria, it sets up the information it wants to discover in addition to the semantics nodes' addresses in the upper level (distance, supported type(s) of semantics resources, etc.) (step 616).

At step 620, the new semantic node may register to the higher level parent semantics node it discovered or otherwise selected. If the new semantic node is unable neither to learn the address of a higher-level semantic node discovery server nor to identify any higher-level parent semantic nodes of its siblings to which it might register, it may determine that no higher level parent semantic nodes are available and end the process at step 612.

Referring back to FIG. 5A, once discovery of siblings and discovery and registration with a parent node is complete, the information about the new semantic node's siblings and parent is stored (step 514). As further illustrated in FIG. 5A, if new siblings join the network or an existing sibling goes offline, the semantic node may update it semantic node relationships (steps 516, 518). At step 520, the new semantic node is now operational. As further illustrated in FIG. 5A, the operational semantic node may at some later point be triggered to register to another higher level node (step 522) of it may leave the network (step 526). In the former case, the semantic node may deregister with its current parent and register with the new one (step 524). In the latter case, the semantic node may simply deregister with its current parent (step 528).

Figure 6:
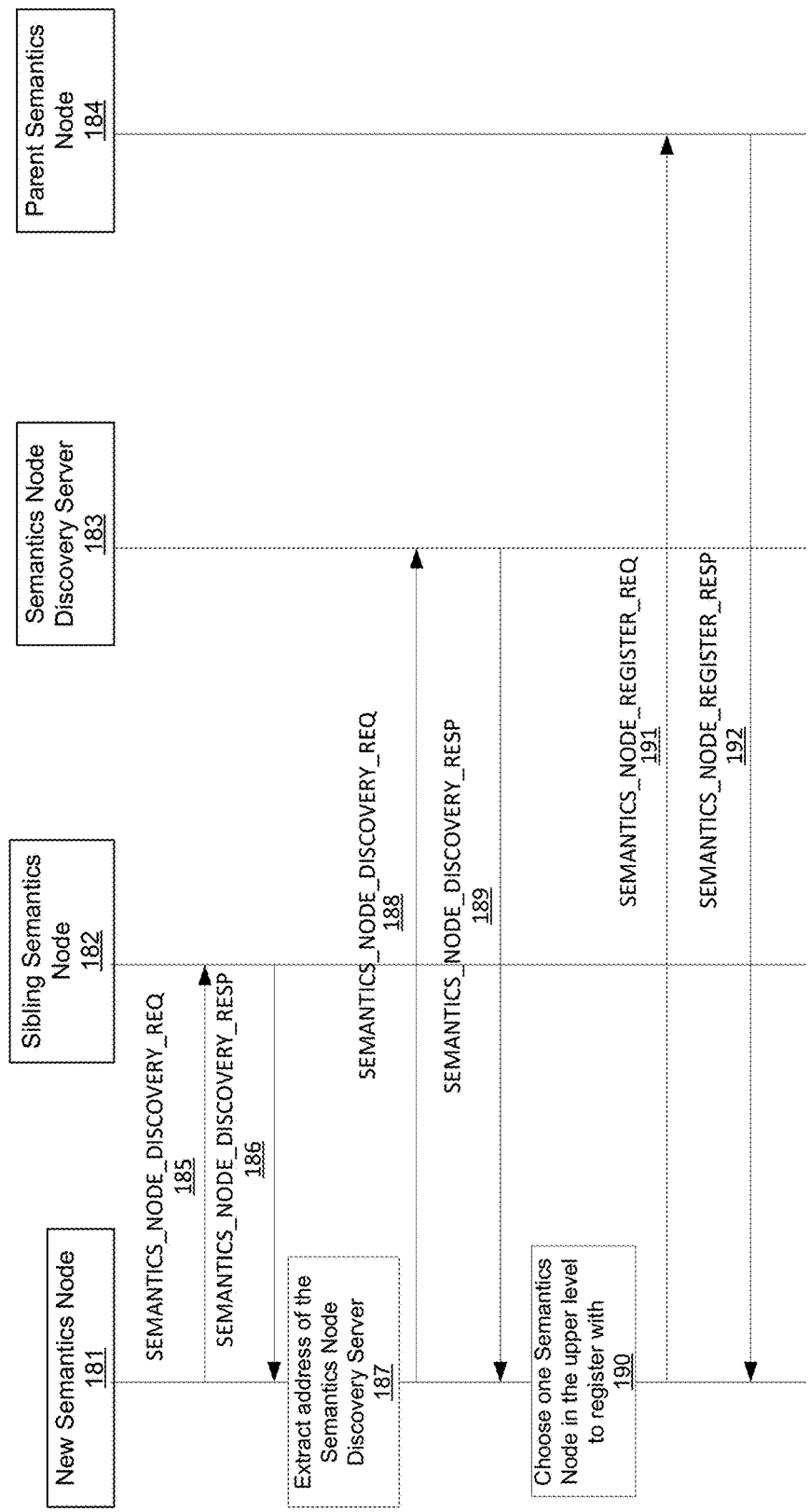
FIG. 6 illustrates a message flow of semantics node registration.

FIG. 6 is a message flow diagram further illustrating the semantics node discovery and registration process discussed above and illustrated in FIG. 5A and FIG. 5B. At step 185, new semantics node 181 sends a semantics node discovery request to sibling semantics node 182. Sibling semantics node 182 is in the same network level as new semantics node 181. The semantics node discovery request of step 185 may contain a request for information (e.g., an address) with regard to semantics node discovery server 183 or information for a semantics node that is the parent (e.g., upper level) semantics node 184 of sibling semantics node 182. A request for the parent semantics node may allow new semantics node 181 to choose its own parent to register with.

Semantics node discovery server 183 may be considered a centralized point for storing information of the semantics nodes scattered in the same level or a rendezvous point to flood the discovery request in the same level of a network and collect the returned responses of semantics nodes. Semantics node discovery server 183 may be a server that resides in a network at a higher, same, or lower level network level than the network level of new semantics node 181. This example assumes that semantics node discovery server 183 is in an upper level in relation to the network level of new semantics node 181. The address of the semantics node discovery server 183 can be well known to lower level semantics nodes (e.g., sibling semantics node 182). If new semantics node 181 is not provisioned with semantics node discovery server 183, then new semantics node 181 may perform sibling semantics node discovery. If new semantics node 181 is provisioned with the address of the semantics node discovery server 183, it can perform the semantics node discovery directly.

At step 186 of FIG. 6, sibling semantics node 182 sends a semantics node discovery response. The semantics node discovery response may contain information (e.g., address information) for semantics node discovery server 183 or information for a semantics node that is the parent of sibling semantics node 182. Each sibling node in a level of a network may respond with parent semantics node information and semantics node discovery server information, which may be different from the information provided by sibling semantics node 182.

At step 187, new semantics node 181 extracts the received address of semantics node discovery server 183. At step 188, new semantics node 181 sends a semantics node discovery request to semantics node discovery server 183. The request at step 188 may be a query for one or more parent semantics nodes that new semantics node 181 may connect with. At step 189, semantics node discovery server 183 sends a semantics node discovery response to new semantics node 181. The response at step 189 may contain one or more parent semantics nodes. At step 190, new semantics node 181 chooses one parent semantics node to register with. At step 191, semantics node 181 sends a request for registration with its chosen parent semantics node 184. At step 192, parent semantics node 184 sends a response to the request for registration at step 191.

Generally, if new semantics node 181 is provisioned with the address of semantics node discovery server 183, it can perform the semantics node discovery directly. Otherwise new semantics node 181 decides whether it wants to choose from the list of parent semantics node received from one or more siblings and whether it wants to retrieve the default address of semantics node discovery server 183 from siblings. At each level, there may be one or more semantics node discovery servers, which accepts the higher-level semantics node discovery request by default. If new semantics node 181 chooses an upper-level semantics node from the siblings' parents, new semantics node 181 may choose not to perform the semantics node discovery further. New semantics node 181 may have the option to decide the criteria of choosing the parent (e.g., choosing from options, such as nearest in hop count, supporting the same type(s) of semantics related resources, etc.). Based on the criteria, new semantics node 181 sets up the information it wants to discover in addition to the addresses of semantics nodes in the upper level (e.g., distance, supported type(s) of semantics related resources, etc.).

Figure 7:
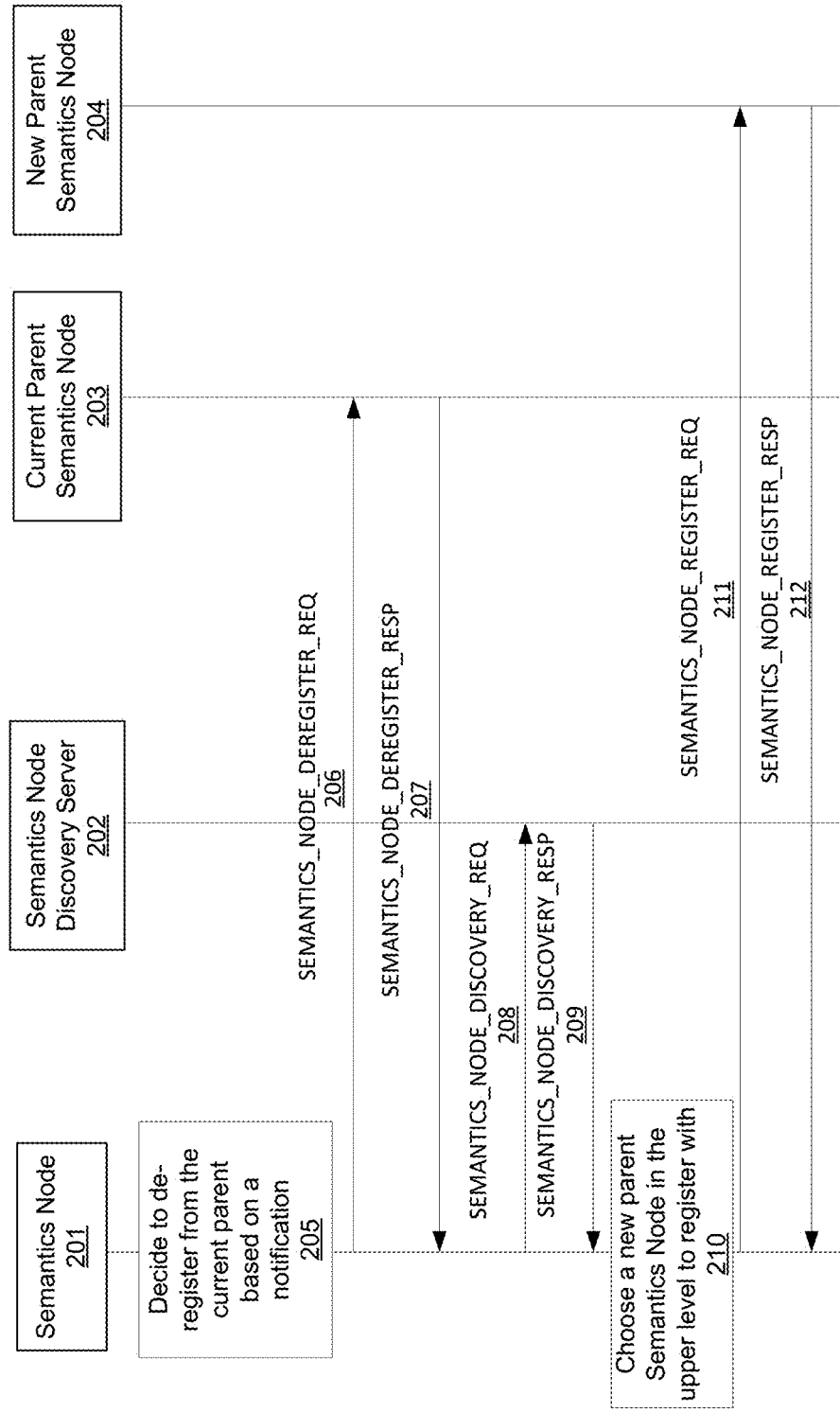
FIG. 7 illustrates a parent-child relationship update initiated by child.

FIG. 7 provides a message flow providing further details of a parent-child relationship update process (e.g., steps 522 and 524 of FIG. 5A), in accordance with one embodiment thereof. The update may be initiated by a child or parent semantics node. At step 205, semantics node 201 decides to de-register from current parent semantics node 203 based on a notification. The notification may be a message from current parent semantics node 203 to initiate de-registration, a determination that current parent semantics node 203 is not reachable (e.g., offline, disconnected, or other communication issue), or a received status update associated with parent semantics node 203 (e.g., network traffic congestion, device or line errors, memory capacity issues, etc.), among other things.

At step 206, semantics node 201 sends a de-register request to current parent semantics node 203, which includes a request to end the parent-child relationship. At step 207, semantics node 201 may receive a response to the de-register request sent in step 206 from current parent semantics node 203 or another device that is able to communicate a perceived status of current parent semantics node 203. Similar to the steps illustrated with regard to FIG. 6, semantics node 201 tries to register with a new parent semantics node. At step 208, semantics node 201 sends a semantics node discovery request to semantics node discovery server 202. At step 209, semantics node discovery server 202 sends a semantics node discovery response to semantics node 201. At step 210, semantics node 201 chooses one upper level semantics node to register with. At step 211, semantics node 201 sends a request for registration with its chosen new parent semantics node 204. At step 212, new parent semantics node 204 sends a response to the request for registration at step 211, which confirms the update of the parent-child relationship.

In an embodiment (not shown, but with reference to elements in FIG. 7), a parent semantics node may trigger the de-registration of a child and provide a new parent semantics node for the child to register with. This new parent information may be included in a de-registration trigger message or alternatively in a separate trigger message. Semantics node 201 can register to new parent semantics node 204 by having current parent semantics node 203 send the registration request to new parent semantics node 204. Current parent semantics node 203 has the option to forward information of semantics node 201 to new parent semantics node 204 for registration purposes. Current parent semantics node 203 or semantics node 201 may terminate the parent-child relationship before switching current parent semantics node 203 to new parent semantics node 204.

Generally, parent-child relationships of semantics nodes are terminated by de-registering to the current parent semantics node when the child semantics node goes offline or when the child semantics node registers to another higher level parent semantics node.

If a neighboring sibling semantics node joins a network, the corresponding sibling information is updated by adding the new semantics node. If a neighboring sibling semantics node leaves a network, the corresponding sibling information is updated by deleting the semantics node or otherwise updating a table to indicate the status of the sibling semantics node that left the network (e.g., status=offline). A semantics node may broadcast or otherwise communicate its status to sibling semantics nodes using, for example, the SEMANTICS_NODE_STATUS_NOTIFY( ) message shown above in Table 1. The status update may affect how a sibling and parent-child relationships are maintained.

B. Semantics Related Resource Discovery, Retrieval, and Validation

Figure 27:
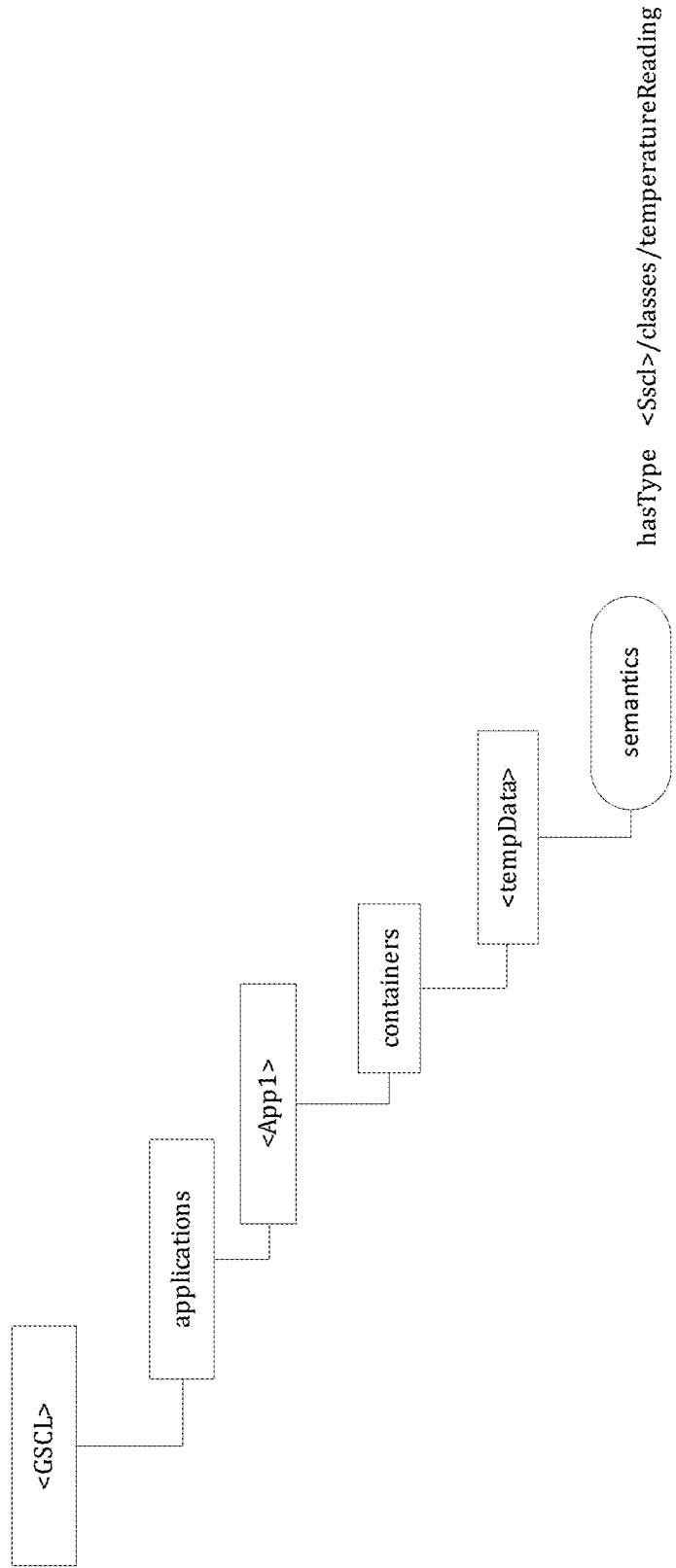
FIG. 27 provides an illustration of one example of the use of semantic nodes as described herein.

An application, a device, a user, a peer semantics node, an external semantics node, or a non-semantics node may send semantics related resource discovery requests to a semantics node through the sIc, sIs, and sIe reference points. The discovery request message may include the type of the semantics related resource (class, relationship, or term) and search string(s). For example, assume a temperature sensing application (App1) in an M2M system that needs to report its temperature reading data—as an integer in units of Celsius—to its M2M gateway. In order to enable the gateway service capability layer (GSCL) to understand the data, App1 needs to associate the data with proper semantics information. In accordance with the procedures described herein, App1 may discover a semantic node that stores a semantic related resource class—the temperatureReading class—that represents temperature data as an integer in units of Celsius. After discovery, App1 will retrieve the representation of the temperatureReading class, and validate that it is the one it wants to use to provide semantics for its temperature data. It will then link the data with the temperatureReading class as one of its attributes (semantics attribute). In the GSCL, the data may be stored under a <tempData> container for App1, which will have a semantics attribute that links to the temperatureReading class using a hasType relationship—as illustrated for example in FIG. 27. As a result, all the App1 data stored under the <tempData> container in the GSCL will have the same semantics—that each item of data is an integer and has the unit of Celsius. As another example, App1 may be an application which retrieves a resource from an NSCL. The resource may have a semantics attribute which links to the temperatureReading class (similar to the above example). In order to understand and interpret the data in a container of the resource, App1 will need to retrieve the semantics-related resource to which the semantics attribute of the resource is linked—in this case the temperatureReading class. After App1 retrieves the representation of the temperatureReading class semantics-related resource, it will be able to interpret the resource data—which it now knows is an integer and has the unit of Celsius.

Figure 8:
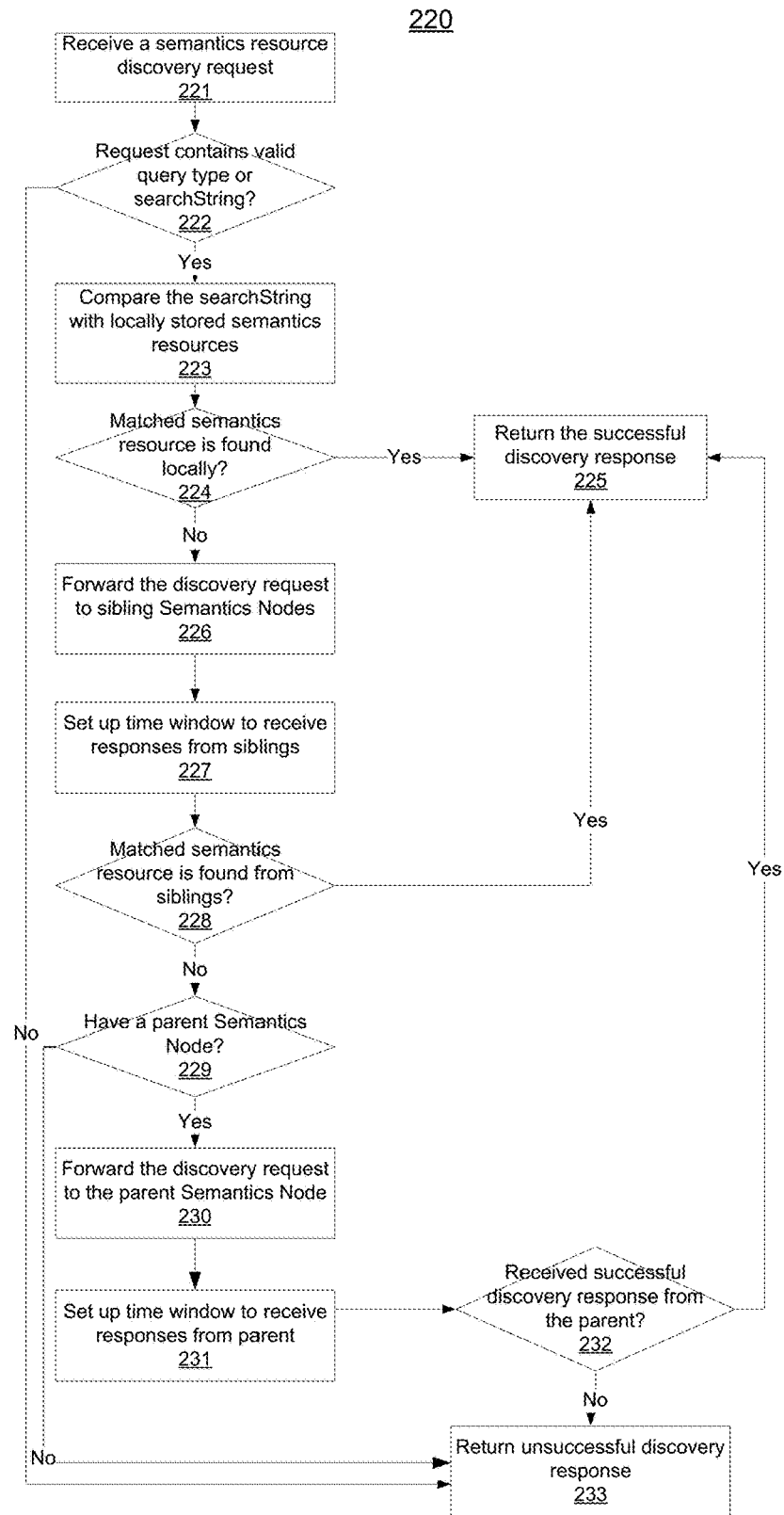
FIG. 8 illustrates a flow diagram of processing semantics resource discovery.

FIG. 8 is flow diagram illustrating the processing of a semantics related resource discovery request at a semantics node, in accordance with one embodiment. At block 221, a semantics node receives a semantics related resource discovery request that includes the type of the requested semantics related resource and potential search string(s). At block 222, the semantics node checks the discovery request. If the request is insufficient or malformed (e.g., missing type of requested resource) the discovery request is considered invalid and an invalid discovery response will be returned to the issuer (e.g., requesting client device) as indicated by block 233. If the request is valid, as indicated by block 223, the search string is compared with locally stored semantics related resources. In particular, based on the type of the requested semantics related resource, the semantics node is able to determine which type (i.e., class, relationship, or term) of semantics related resource on which it will search. As indicated by block 224, using the search string(s) as a key word(s), the semantics node searches its local semantic database to find one or more matching semantics related resources. If there is a matching semantics related resource found locally, the address (e.g., URL/URI) of the semantics related resource is returned to the issuer in a discovery response, as indicated by block 225.

If there is not a matching semantics related resource found locally, the semantics node will try to find a matching semantics related resource from its sibling semantics nodes. As indicated by block 226 and block 227, the semantics node forwards the discovery request to the siblings and sets up a time window it will wait for the response to come back. At block 228, it is determined whether a matching semantics related resource is found from the contacted siblings. If matching semantics related resources are returned from its siblings, the corresponding address (e.g., URI/URL) of the semantics related resource(s) is sent back to the issuer with a successful discovery response (block 225).

If there are no matching semantics related resources returned from siblings of the semantics node, then it is determined whether a parent semantics node can be contacted, as indicated by block 229. If there is no parent semantics node, then a discovery response indicating a negative outcome will be returned to the issuer (block 233). If there is a parent semantics node, the semantics node will try to find a matching semantics related resource from its parent semantics nodes. As indicated by block 230 and block 231, respectively, the semantics node forwards the discovery request to the parent semantics node and sets up a time window it will wait for the response to come back. At block 232, it is determined if a matching semantics related resource is found from the contacted parent. If matching semantics related resources are returned from the contacted parent, the corresponding address (e.g., URI/URL) of the semantics related resources is sent back to the issuer with a successful discovery response (block 225). If there are no matching semantics related resources returned from the parent of the semantics node, then a discovery response indicating a negative outcome will be returned to the issuer (block 233).

After the issuer receives a successful discovery response, which contains the address (e.g. URL/URI) of the matching semantics resource, the issuer can retrieve the representation of the semantics resource.

In one embodiment, the semantics node may support a RESTful architecture style (representational state transfer), which consist of clients and servers. Clients (e.g., Issuers) initiate semantic requests to servers (e.g., semantics nodes). In this embodiment, servers (e.g., semantics nodes) process requests for semantics and return appropriate semantic responses. Requests and responses are built around the transfer of representations of semantics related resources. A client can be an application, a user, a device, a semantics node, etc, which can request RESTful operations on the semantics related resources (e.g., classes, relationships, or terms) to a semantics node.

When handling resources in a RESTful architecture, there are four basic methods that may be applied to the semantic related resources:

CREATE: Create a class, relationship, or term resource.

RETRIEVE: Read the content of a class, relationship, or term resource.

UPDATE: Write the content of a class, relationship, or term resource.

DELETE: Delete a class, relationship, or term resource.

A semantics node acting as a RESTful server may validate a received request. The operation is allowed, if the issuer is authorized with the proper access rights.

Figure 9:
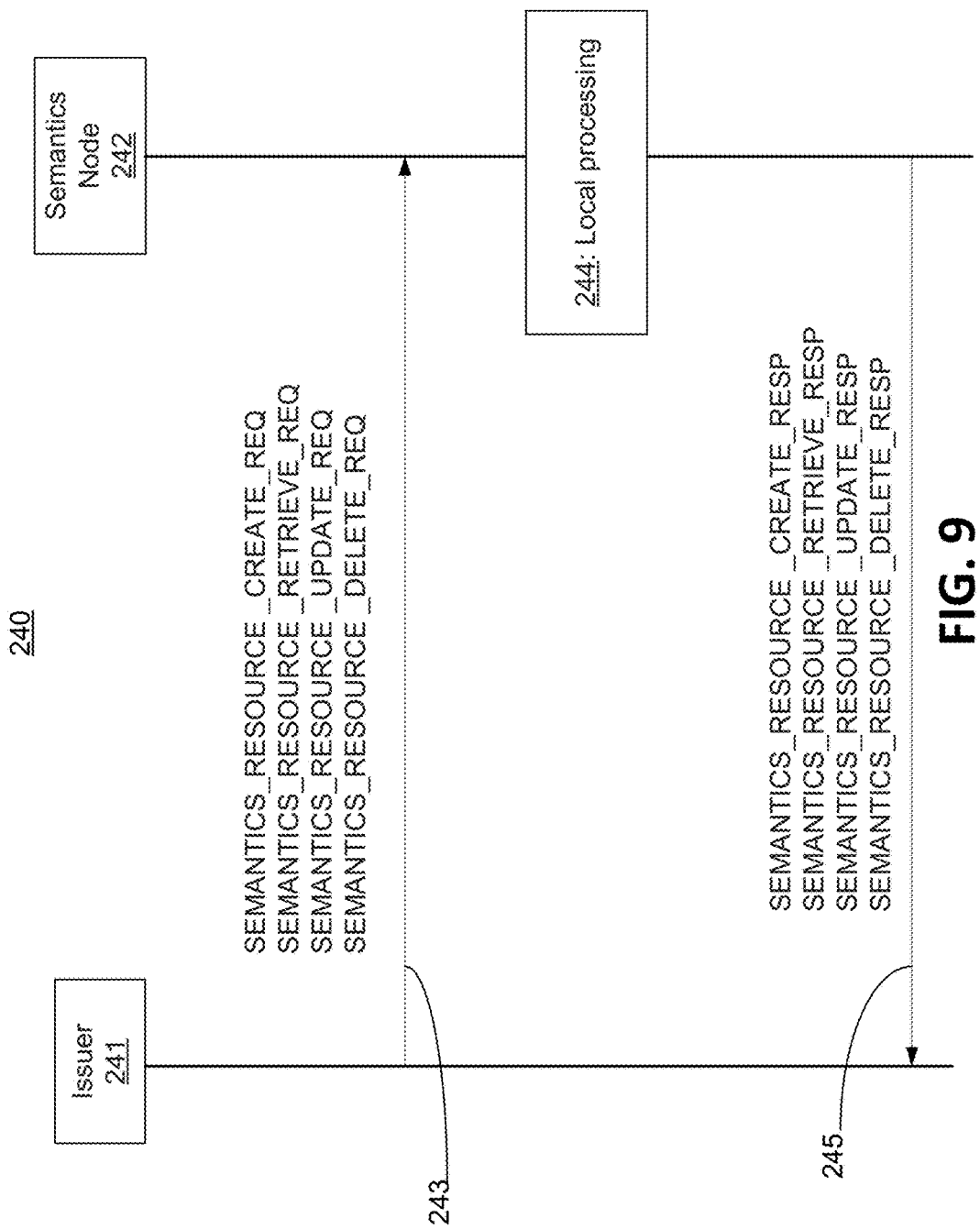
FIG. 9 illustrates a message flow of RESTful semantic node operations.

FIG. 9 is a message flow diagram further illustrating these RESTful semantic node operations in accordance with this RESTful embodiment. At step 243, issuer 241 requests to create, update, retrieve, or delete a semantics related resource (a class, relationship, or term) using the RESTful CREATE, UPDATE, RETRIEVE, or DELETE verbs correspondingly. Issuer 241 may be an application, another semantics node, a device, a user, or the like. To create a semantics related resource at step 243, issuer 241 issues a CREATE request, providing the type and representation of the semantics related resource. To update a semantics related resource at step 243, issuer 241 issues a UPDATE request, providing the unique identity or address and the updated or partially updated representation of the semantics related resource. To retrieve a semantics related resource at step 243, issuer 241 issues a RETRIEVE request, providing the unique identity or address of the semantics related resource and optionally a searchString parameter(s). To delete a semantics related resource at step 243, issuer 241 issues a DELETE request, providing the unique identity or address of the semantics related resource.

At step 244, semantics node 242 acts as a server and validates and otherwise processes the received request. The received request is allowed, if issuer 241 is authorized with the proper access rights. If the create operation is allowed by the semantics node 242, the new semantics related resource is created under the proper resource pool based on whether it is a class, relationship, or term. And the semantics related resource is assigned a unique identity or address by semantics node 242. If the update operation is allowed by semantics node 242, the representation of the semantics related resource is updated. If the retrieve operation is allowed by semantics node 242, the representation of the semantics related resource is prepared in the format issuer 241 requests. If the delete operation is allowed by semantics node 242, the requested semantics related resource is deleted.

At step 245, semantics node 242 returns a response to issuer 241. For a create operation, the identity or address of the newly created semantics related resource is returned to the issuer. For an update operation, a response code is returned to issuer 241 whether the operation is successful or not. For a retrieve operation, the representation of the semantics related resource in a format issuer 241 requests are returned to issuer 241. For a delete operation, a response code is returned to issuer 241 to indicate whether the operation is successful or not.

Figure 10:
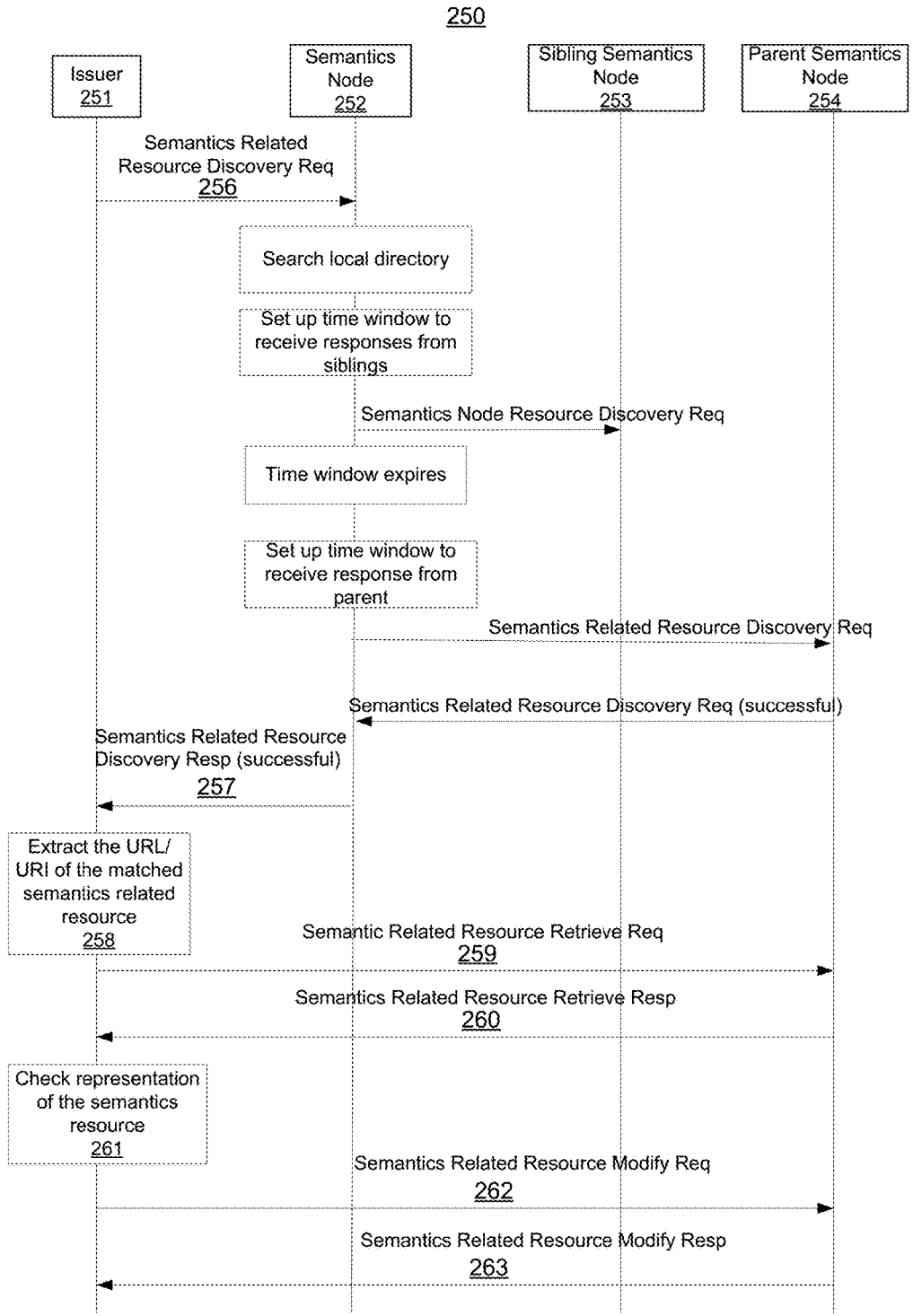
FIG. 10 illustrates a message flow of the semantics related resource discovery, retrieval and validation process.

FIG. 10 is a message flow 250 further illustrating the semantics related resource discovery, retrieval, and validation process described herein. In this example, a network may contain issuer 251, semantics node 252, a sibling semantics node 253 which is a sibling of semantics node 252, and a parent semantics node 254 which is a parent to semantics node 252. At step 256, issuer 251 sends a semantics related resource discovery request to semantics node 252. As shown in message flow 250, semantics node 252 goes through several steps (similar to the process in FIG. 8) to find a semantics related resource(s) that matches the request at step 256. As illustrated, first the semantics node 252 will search its local directory. If it does not find any matching resources, it will set up a time window and forward the discovery request to its siblings, such as sibling 253. If no responses are received from its siblings, the semantics node 252 may forward its request to parent semantics node 254. In this example, it is assumed that the parent semantics node 254 does find a matching resource, and it will send a response back to the semantics node 252 indicating the address (e.g., URI/URL) of the semantics related resource(s) that it found.

At step 257, semantics node 252 then sends a semantics related resource discovery response back to the Issuer 251, which includes the address (e.g., URI/URL) of the semantics related resource(s) from the parent semantics node 254 that matched the Issuer's request. At step 259, issuer 251 sends a semantics related resource retrieve request based on the received URL. At step 260, parent semantics node 254 sends a semantics related resource retrieve response that contains the requested semantics information which may include a class, relationship, or term.

At step 261, issuer 251 checks (validates) the representation of the received semantics information from step 260. There is a possibility that the received semantics related resource sent at step 260 is not exactly what issuer 251 wants. For example, if issuer 251 requested a temperature class and the returned matching resource is a class called temperatureReading with an associated unit of Fahrenheit, but issuer 251 desires a temperature class with unit of Celsius, then issuer 251 can request that parent semantics node 254 modify the semantics. This can be supported by sending a semantics related resource modify request at step 262 to parent semantics node 254 to modify the semantics related resource. At step 263, the address (e.g., URL/URI) of the newly added or modified semantics related resource will be returned to issuer 251.

With reference to modification of semantics related resources, generally, the semantics node may collaborate with its siblings or parent to perform the modification, if the semantics node does not support modification itself. If the semantics node supports modification, then the semantics node may modify the class locally by adding a new class or extending the current one.

C. Subscribing to Semantics Related Resources

In one embodiment, a semantics node can support a client (e.g., an application, another semantics node, a device, a user, or the like) subscribing to it. As one example, a client may subscribe to the semantic node to be notified when any update to a subscribed semantic related resource. When an update occurs, the subscribing client will be notified with the new representation of the resource. In the case of a client that is a semantic node itself, the subscribed semantics related resource might be stored in another semantics node that the subscriber semantics node has no relation with (e.g., not a parent-child or sibling). In this example, a client may issue a SEMANTICS_RESOURCE_SUBSCRIBE_REQ message to a semantics node. The message identifies the semantics related resource for which the client wishes to receives notifications when the resource is updated. The semantics node will respond to the request with a SEMANTICS_RESOURCE_SUBSCRIBE_RESP message acknowledging the subscription. When the semantics related resource to which the client has subscribed is updated, the semantics node will send a SEMANTICS_RESOURCE_SUBSCRIBER_NOTIFY message to notify the client of the update.

Figure 11:
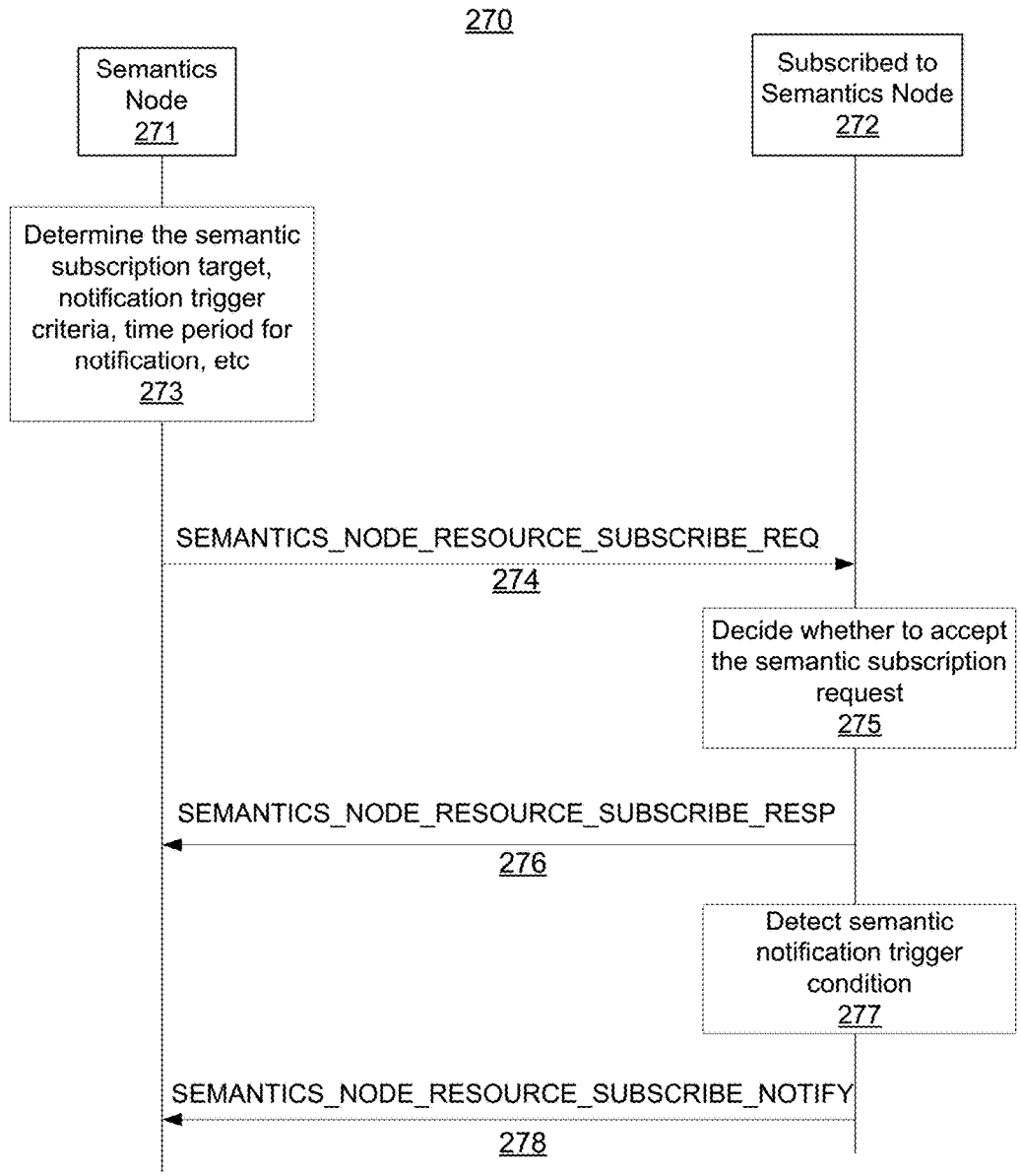
FIG. 11 illustrates a flow diagram of a semantics node that may be updated with the semantics related resources stored and managed by a sibling/parent/child semantics node.

As another example, a semantics node may be interested in being updated with the semantics related resources stored and managed by one of its sibling, parent, or child semantics nodes. FIG. 11 is an exemplary flow 270 of a subscription/notification process for this situation, in accordance with one embodiment. In this example, a semantics node 271 is updated with the semantics related resources stored and managed by a subscribed-to semantics node 272. Subscribed-to semantics node 272 may be a sibling, parent, or child of semantics node 271. At step 273, semantics node 271 identifies the subscription target and may set up notification trigger criteria such that it only receives semantics related resource notifications relevant to the trigger criteria. For example, the subscriber may configure the notification trigger criteria to specify a particular semantics related resource or a particular number of updates to a semantics related resource before a new notification is sent. Semantics node 271 may also set up the time period scheduling information for when the notification should be sent.

At step 274, semantics node 271 sends a semantics node resource subscribe request to the target semantics node 272. At step 275, the target semantics node 272 determines whether to accept the semantics subscription request of step 274. to the target semantics node 272 can decide whether to accept a subscription request, based on the existing subscribers, load of handling the subscription (e.g., load with regard to collecting update information or bandwidth used to send a notification), etc. At step 276, the target semantics node 272 sends a semantics node subscription response to semantics node 271. The response at step 276 may include confirmation of the subscription and parameters that will be used in processing the subscription. At step 277, at some point in time after step 276, the target semantics node 272 detects a semantic notification trigger condition that matches the requested trigger received at step 274. At step 278, the target semantics node 272 sends a semantics node resource subscribe notify message to update semantics node 271 with regard to a particular semantics related resource.

Generally, a semantics related resource subscription can facilitate the semantics related resource discovery from a peer semantics node or parent semantics node. For example, based on the notification messages (which would include the URIs of newly created or updated semantics related resources stored on a semantics node), a semantics node may be able to perform discovery on semantics related resources of other nodes without sending discovery requests.

D. Linking and Association to Semantics Related Resources

The semantics related resources of a semantic node can be used in various ways. For example, semantics related resource representations may be retrieved from a semantics node and may be stored in a co-located manner in a network location where the data is stored (e.g., on a network server, on a device, on a gateway, etc). Alternatively, the semantics of a resource may be stored on a semantic node and a link to the semantics may be co-located and stored along with the data. This semantic link may be stored in-line (i.e., embedded) within the data or may be stored separately (e.g. in a separate resource or attribute) alongside the data. Thus, through this linking to semantics-related resources, semantics can be applied to normal resources in an M2M system (e.g., <SCL>, <application>, <container> etc.). Typically, this linking will be created by the resource creator/generator, when the resources are created.

Continuing with the earlier example of a patient health monitoring application in FIG. 1, there are semantic classes defined on a semantics node and the URLs of these classes may be discovered by a patient health monitoring application. Table 2 shows examples of semantics related resources of type "class" that are relevant to the patient health monitoring application. Data may be linked to these semantic classes using a semantic relationship called hasType. As a result, for each data resource with a URI of example/healthmonitoring/data1, the semantics of the resource will be known by the following associations:

| example/health/patient/data1 | hasType | semanticsNode1/class/patient |
| example/health/doctor/data2 | hasType | semanticsNode1/class/doctor |
| example/health/bp/data1 | hasType | semanticsNode1/class/bloodpressure |
| example/health/temp/data1 | hasType | semanticsNode1/class/temperature |
| example/health/hr/data5 | hasType | semanticsNode1/class/heartrate |

The hasType relationship may also be identified by a URL/URI which references a semantic description of the hasType relationship stored on the semantic node.

TABLE 2

Example of Class Semantics Related Resources

| Class | Fields | URL |
| --- | --- | --- |
| Patient | Name: String<br>Sex: F/M<br>Address: String<br>Disease: String | semanticsNode1/class/patient |
| Doctor | Name: String<br>Affiliated hospital: String<br>Specialty: String | semanticsNode1/class/doctor |
| Blood_Pressure | Systolic Pressure: mmHg<br>Diastolic Pressure: mmHg | semanticsNode1/class/bloodpressure |
| Temperature | Unit: Fahrenheit | semanticsNode1/class/temperature |
| Heart_Rate | Unit: bpm | semanticsNode1/class/heartrate |
| . . . | | |

E. Grouping Optimization

If a group of resources have some similar semantics (e.g., all resources in the same application have the same semantics), the similar semantics may be applied to the application, instead of to each individual resource under that application. FIG. 12 illustrates a method 281 of grouping of resources with the same semantics, in accordance with one embodiment thereof. At step 281, some of the existing data of the same application is determined to share the same semantics association. At step 282, the determined data in the same application sharing the same semantics is classified into groups. At step 283, each group of step 282 is associated with the appropriate semantics. At step 284, newly received data from the same application is put into the group that shares the same semantics. The existing data of the same application may be classified into multiple groups, each of which shares the same semantics linking and association. If new data is generated from the same application, the data is put into the group that shares the same semantics.

For example, multiple instances of blood pressure monitoring data have the same semantics. Hence each instance may be associated with the same semantics (semanticsNode1/class/bloodpressure) as shown below:

| example/health/bp/data1 | hasType | semanticsNode1/class/bloodpressure |
| example/health/bp/data2 | hasType | semanticsNode1/class/bloodpressure |
| example/health/bp/data3 | hasType | semanticsNode1/class/bloodpressure |
| . . . | | |

By supporting this grouping optimization, the following association may also be valid:

| | | |
|---|---|---|
| example/health/bp | hasType | semanticsNode1/class/bloodpressure |

F. Pushing Semantics Related Resources

As mentioned above, the classes, relationships, and terms that are hosted in a semantics node may be discovered and used by others. Based on the frequency of the requests, some of the semantics related resources may be pushed or mirrored in another semantics node for easier discovery and access. For example, after one semantics node detects the same forwarded discovery request from another semantics node a certain number of times (e.g., exceeding a policy defined threshold); it may decide to push a mirrored copy of the semantics related resource to that semantics node.

Figure 13:
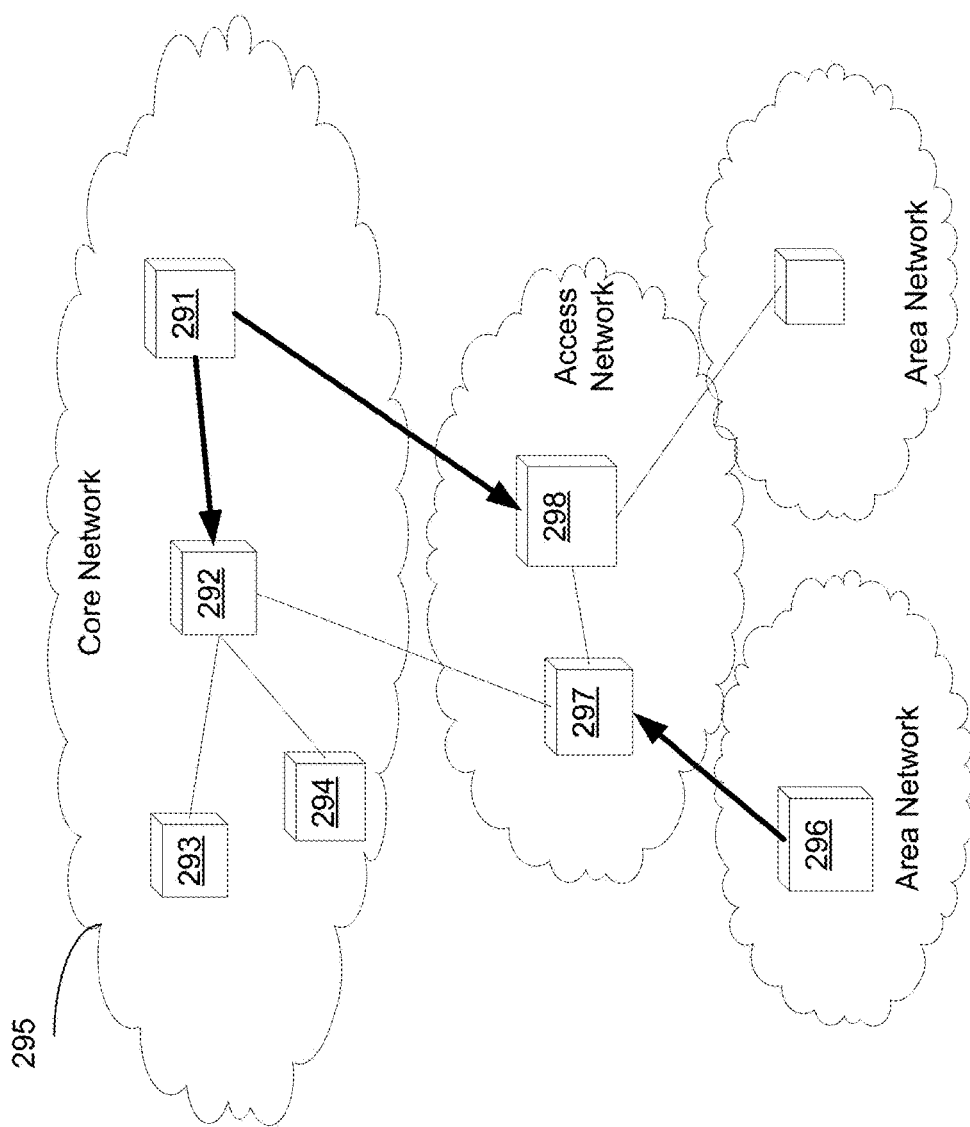
FIG. 13 illustrates a semantics related resource pushing.

The semantics related resource pushing can happen between siblings, or between parent and child semantic nodes, as shown in FIG. 13. For example, semantics node 291 of FIG. 13 in the core network 295 may receive many discovery and retrieval requests for the same semantics related resource (e.g., temperature) from semantics node 292, semantics node 293, and semantics node 294. When discovery requests reach a defined threshold, semantics node 291 may decide to create the same semantics related resource (i.e., mirror the resource) on semantics node 292, such that semantics node 293 and semantics node 294 may access the semantics related resource with a faster response time. The semantics node 291 may create the mirrored resource on the semantics node(s) by issuing a SEMANTICS_RESOURCE_CREATE_REQ message to the other semantics nodes, which would then respond with an appropriate SEMANTICS_RESOURCE_CREATE_RESP message.

The following options may be used in order to keep the semantics related resource up-to-date. With reference to FIG. 13, semantics node 291 may automatically update a semantics related resource on semantics node 292, if there is any update to the original representation of the semantics related resource (e.g., a subscription is not needed). Alternatively, semantics node 292 may subscribe to the original semantics related resource. Based on the subscription of semantics node 292 to the semantics related resource, semantics node 292 will be notified of any change to the particular subscribed to semantics related resource. There also may be a combination of the aforementioned scenarios. For example, there may be a situation where the automatic updates of semantics node 291 occur periodically for all semantics related resources on semantics node 291, while semantics node 292 desires a more immediate update for particular subscribed to semantics related resources.

The semantics related resource pushing can happen between siblings, or between a parent and child in either direction. For example, with reference to FIG. 13, semantics node 296 may push some local semantics related resource to its parent semantics node 297. In another example, semantics node 291 may push some higher-level semantics related resource to its child semantics node 298.

G. Data/Semantics Related Resources Movement

Figure 14:
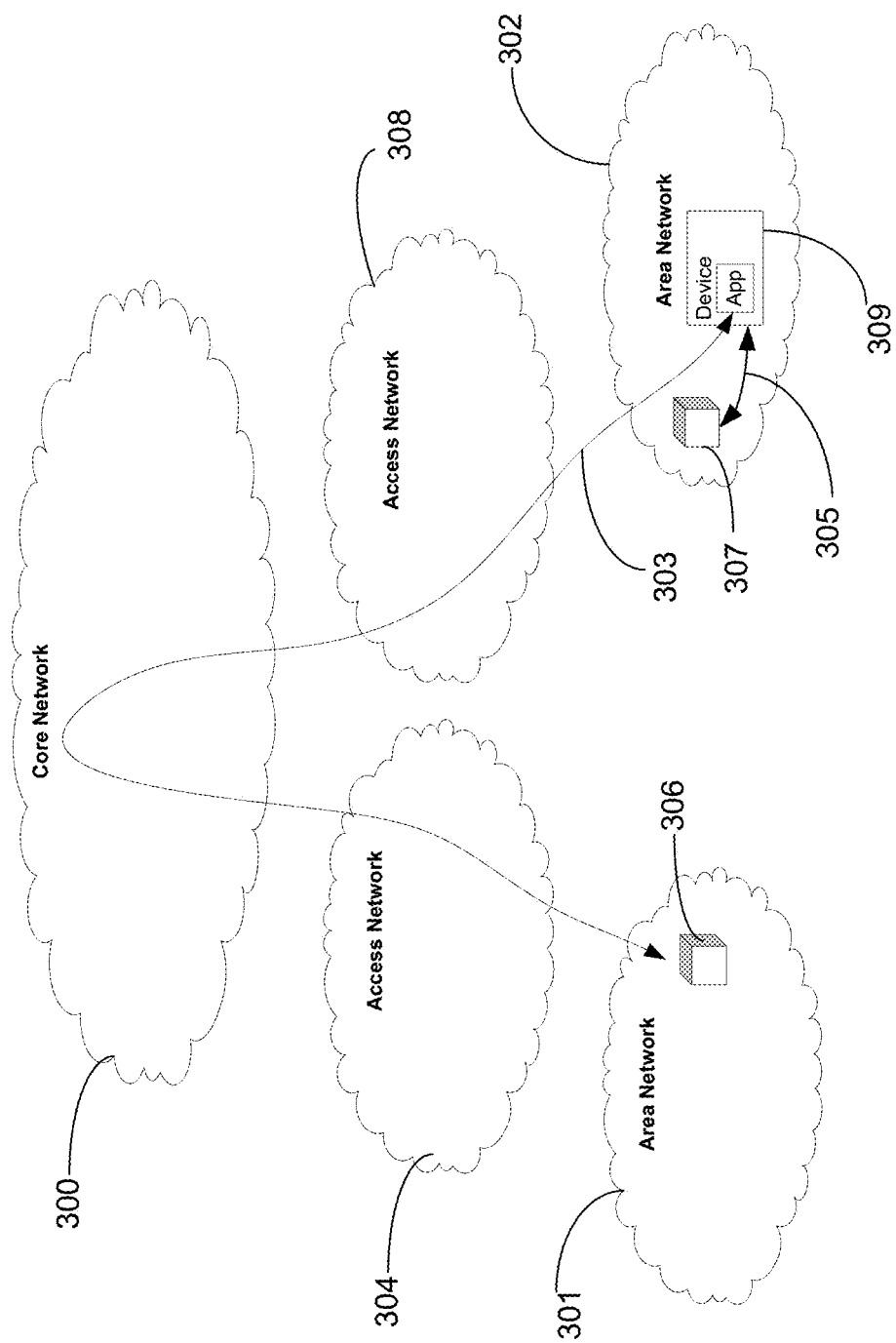
FIG. 14 illustrates a scenario in which a device moves from one area network to another one.

FIG. 14 illustrate a scenario in which a device moves from one network to another. In this scenario, the semantics resources relevant to the device and the data generated by the device may also need to be moved to the new location for security, overhead and/or loading due to the semantics resource retrieval.

Referring to FIG. 14, the device initially may have been located in area network 301, but has now moved to area network 302. Initially, device 309 communicated with semantics node 306. After device 309 arrives at area 302, device 309 may initially continue to communicate to semantics node 306, as demonstrated by line 303. This can result in unnecessary overhead in access network 304, access network 308, and core network 300. To address this and other issues, semantics related resources of semantics node 306 may be moved to semantics node 307 in area network 302. After moving semantics related resources to semantics node 307, device 309 does not need to traverse core network 300 for the semantics related resources but instead can now communicate with semantics node 307 as indicated by line 305.

Figure 15:
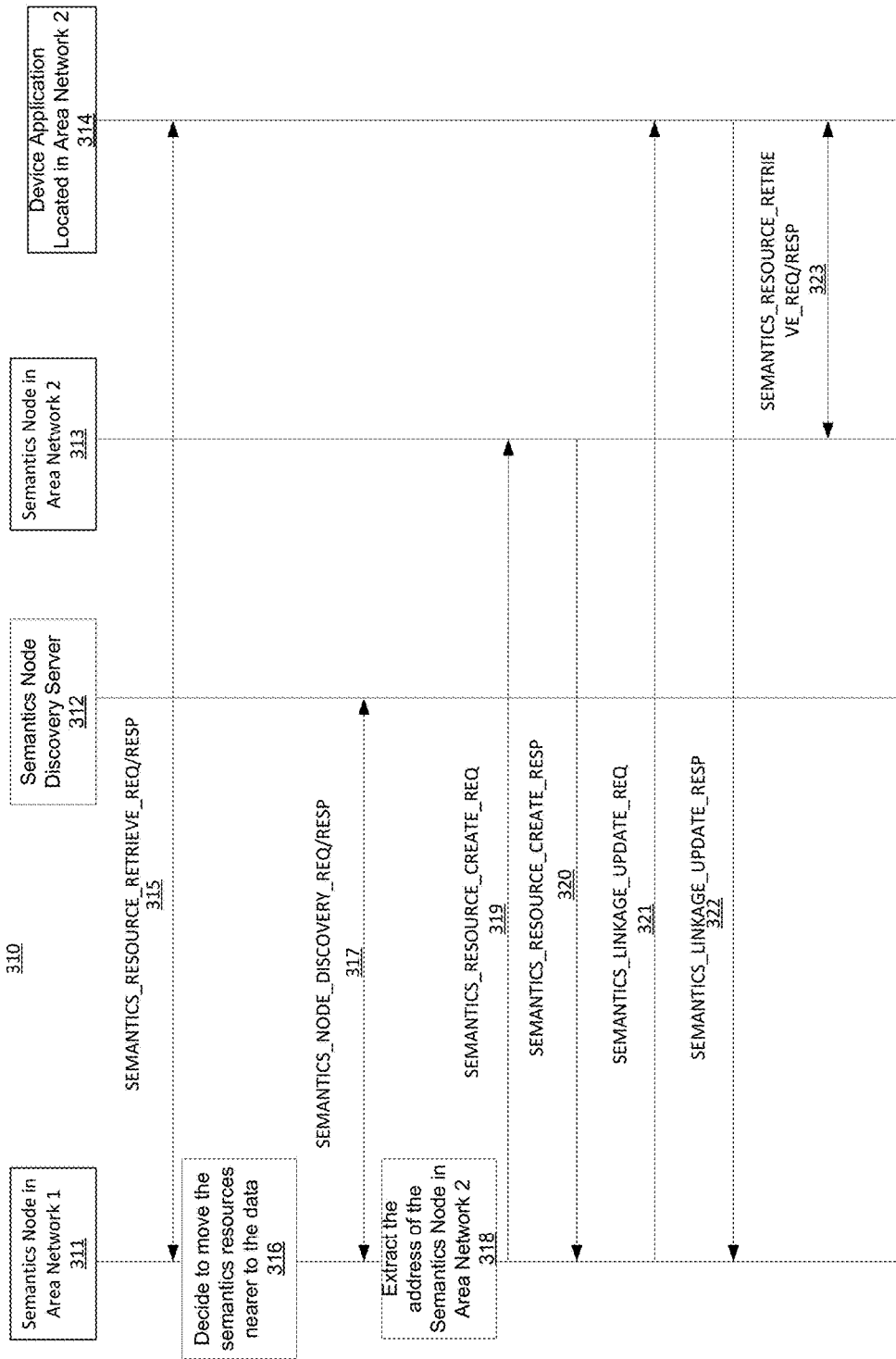
FIG. 15 illustrates a message flow of data/semantics related resources movement.

FIG. 15 is an example message flow 310 further illustrating the movement of data or semantics related resources as depicted in FIG. 14. At step 315, semantics node 311 in a first area network exchanges messages with device application 314 located in area network 2. The messages exchanged at step 315 may include, for example, a semantics related resource retrieve request and semantics related resource retrieve response. At step 316, semantics node 311 decides to move the semantics related resources associated with device application 214 to semantics node 313 located in a second area network. Semantics node 313 may be communicatively closer (takes less time to reach) than the first area network or logically closer (e.g., less hops). With reference to step 316, other devices may make the decision to move the semantics related resources, such as semantics node discovery server 312, device application 314, or another computing device (not shown).

At step 317, semantics node discovery requests and responses are exchanged between semantics node 311 and semantics node discovery server 312 in order to build the hierarchy of semantics nodes, as well as sibling relationships. At step 318, semantics node 311 determines the address of semantics node 313. At step 320, a semantics related resource create request message is sent to semantics node 313 in order to copy the semantics related resource (and other data) that is used by device application 314. Semantics node 313 responds with a semantics related resource create response message, which may include an acknowledgement that the semantics related resource and other data has been copied successfully. At step 321, a semantics linkage update request message is sent to device application 314. The message at step 321 may include instructions for device application 314 to retrieve semantics related resources from semantics node 313. At step 322, the semantics linkage update response message may include an acknowledgement that the semantics node linkage is updated. At step 323, device application 314 retrieves semantics related resources in types of class, relationship, and term from semantics node 313.

V. ETSI M2M/oneM2M Embodiments

A. ETSI M2M Architecture with Semantics Node

Figure 16:
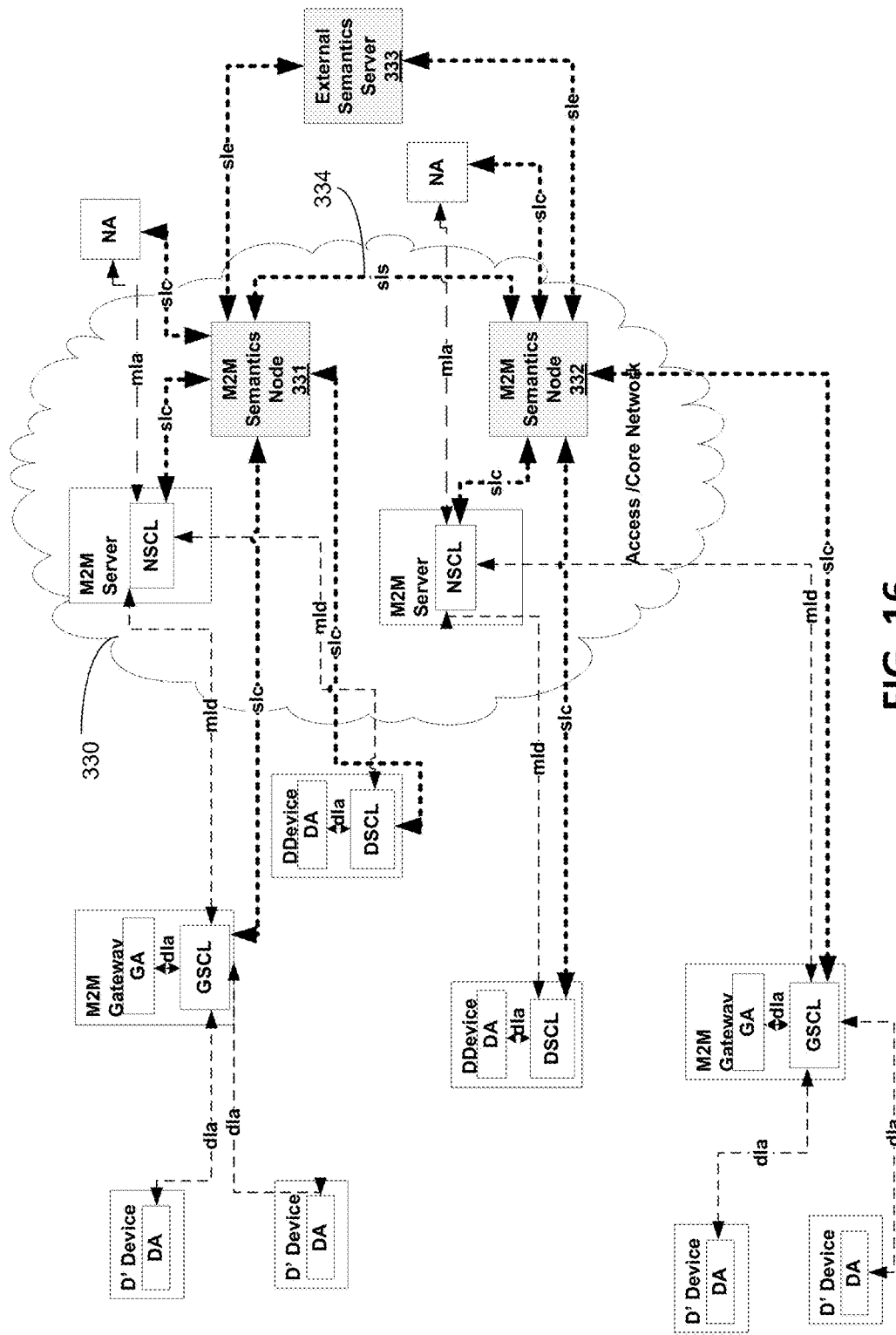
FIG. 16 illustrates a ETSI M2M architecture with stand-alone semantics nodes.

As mentioned above, the semantic node concept described herein can be used to enhance the ETSI M2M architecture. In one embodiment, one or more semantics node may be located in the access/core network as a stand-alone network entity, which may be referred to as a M2M semantics node as shown in FIG. 16. In FIG. 16, M2M semantics node 331 and M2M semantics node 332 are located in the same access/core network 330. M2M semantics nodes in area/core network 330 may interface with DSCLs, GSCLs, NSCLs, and applications via the sIc reference point described above. In addition, M2M semantics node 331 and M2M semantics node 332 may interface with one another via the sIs reference point 334. M2M semantics node 331 and M2M semantics node 332 may also reference to another type of external semantics node 333 via sIe reference points. In this embodiment, M2M semantics nodes located in the access/core network 330 may also form sibling and/or parent-child relationships.

Figure 17:
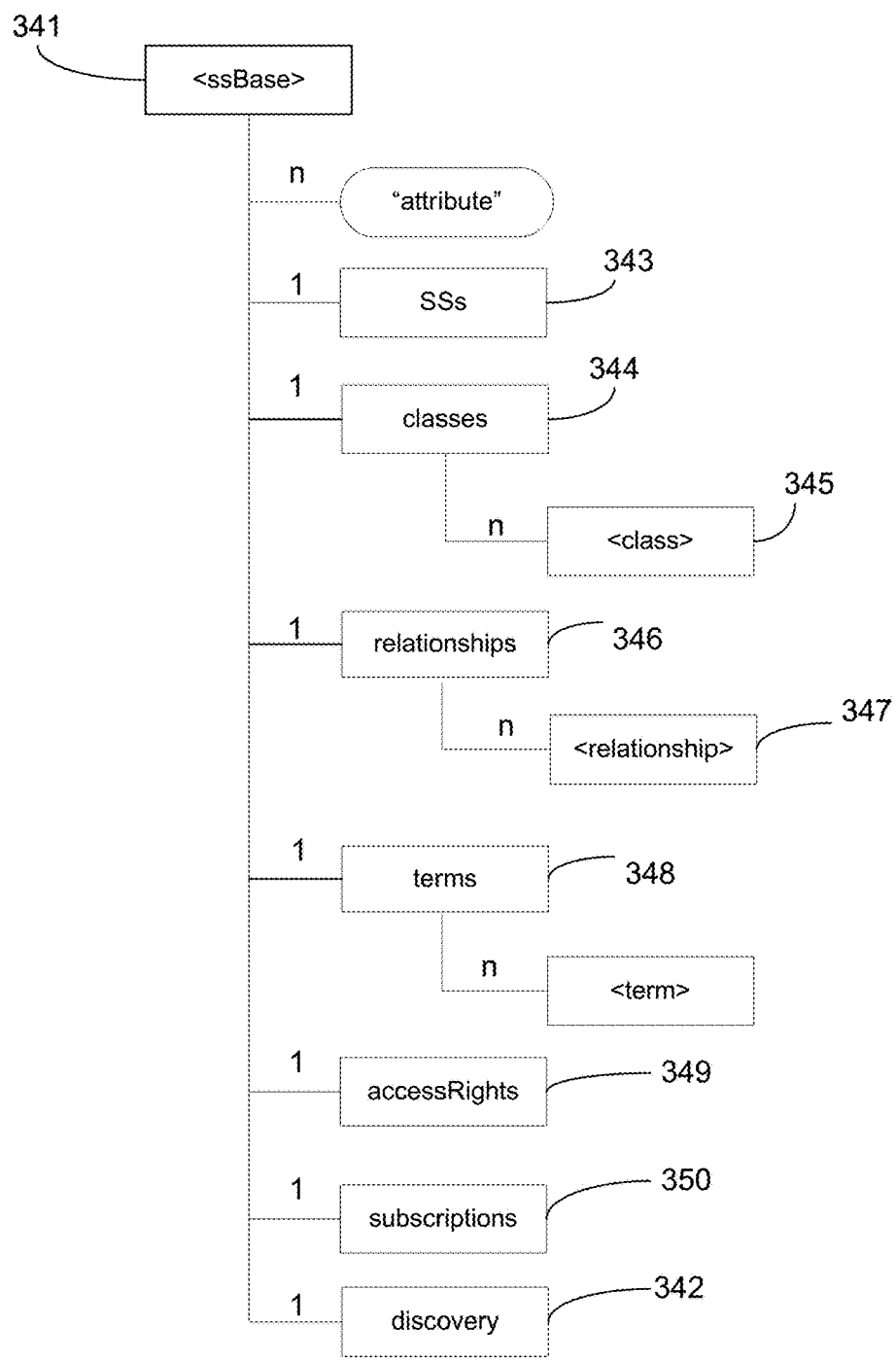
FIG. 17 illustrates a semantics node resource structure.

A semantics node may support a complementary resource structure as used in the service capability layer (xSCL) of the current ETSI M2M Architecture, and this resource structure may be applied to the semantics node described herein, in the manner illustrated in FIG. 17. In this embodiment, the <ssBase> resource 341 is the root of the resource tree residing on the hosting semantics node. The <ssBase> resource 341 may contain attributes that describe the hosting semantics node. The <ssBase> resource 341 contains collection resources representing collections of SS resources 343, classes resources 344, relationships resources 346, terms resources 348, accessRights resources 349, and subscriptions resources 350, among others. Under a classes resource 344 there might be other <class> resources 345, which are the subclasses of the classes resource 344. Under a relationship resource 346 there might be other <relationship> resources 347, which are the sub-relationships of the relationship resource 346. The SSs resource collection 343 contains semantics node resources that are created or deleted when a remote semantics node registers or de-registers with the local semantics node.

Figure 18:
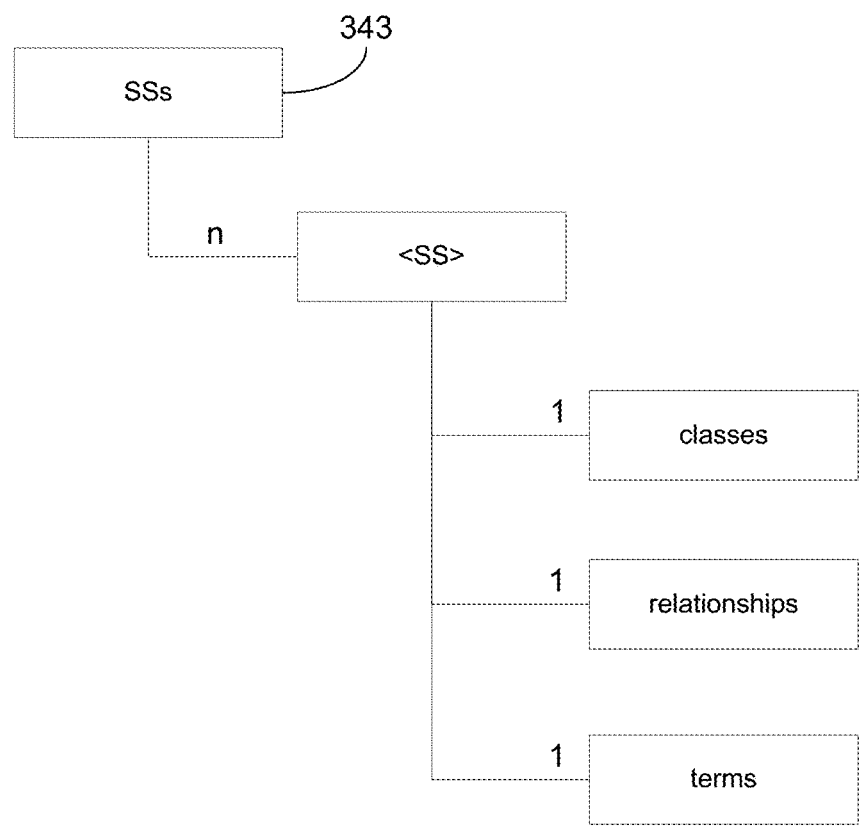
FIG. 18 illustrates a SSs resource structure.

As shown in FIG. 18, each semantics node resource in a collection for SSs resource 343 may have a corresponding resource structure. These resources maintain state for remote semantics nodes registered to the local semantics node. For example, state such as contact address information, discovery information (e.g., announced semantic class, representation, and term resources), and security information (e.g., credentials used to communicate with the corresponding remote semantics node).

With reference again to FIG. 17, the classes 344, relationships 346, and terms 348 collections under <ssBase> resource 341 can each contain respective instances of semantics related resources hosted on the local semantics node. Each instance can contain a semantic representation as well as have other attributes associated with it, such as discovery related information such as tags. These collections of semantics related resources can be accessed by clients having the proper access rights to do so. The accessRights resource 349 under <ssBase> resource 341 can contain instances of accessRight resources. These accessRight resources 349 can define the instances of accessRights that control which clients are granted access to which semantics related resources and operations supported by the semantics node. Alternatively, other instances of accessRights collections can be supported in the resource structure to provide finer grain access controls (not shown in FIG. 17). The collection of subscriptions resources 350 can contain instances of subscription resources. Instances of subscription resources can be created by clients who wish to receive semantic notifications from the semantics node when specified notification trigger criteria events occur. The discovery resource 342 supports client semantic discovery requests. These discovery requests can support search criteria (e.g., semantic related resources having specific types of attributes). The semantics node can respond to discovery requests with a list of resource addresses (e.g., URIs) that match the search criteria (if any). The semantics node can also support forwarding of requests to other semantics nodes (e.g., forwarding of discovery requests to child, sibling, or parent semantics nodes).

B. xSCL with Semantics Capability

Figure 19:
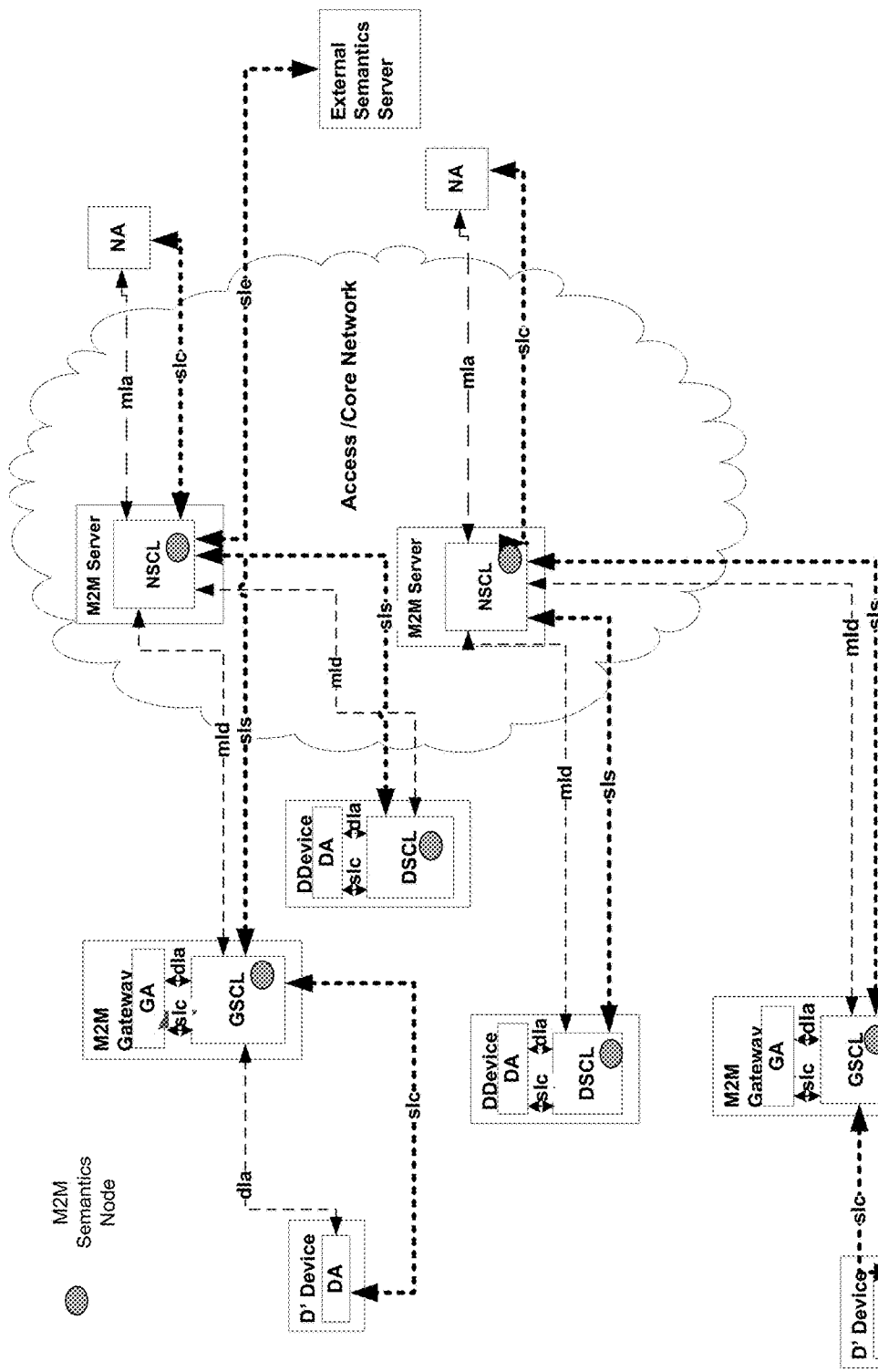
FIG. 19 illustrates a ETSI M2M architecture with integrated semantics nodes.

In another embodiment illustrated in FIG. 19, an M2M semantics node may be deployed as an embedded capability within a DSCL, GSCL, and/or NSCL of the ETSI M2M architecture rather than as a separate standalone semantics node. In this embedded embodiment, the sIs reference point may remain separate or the ETSI M2M mId reference point may be enhanced to support sIs functionality. Likewise, the sIc reference point may remain separate, or the ETSI M2M mIa and dIa reference points may be enhanced to support sIc functionality. In this embodiment, M2M semantics nodes located in the GSCL or DSCL may establish parent-child relationships with the NSCL(s) they are registered with. In addition, the semantics nodes located in GSCLs or DSCLs may also establish sibling relationships with one another.

Figure 20:
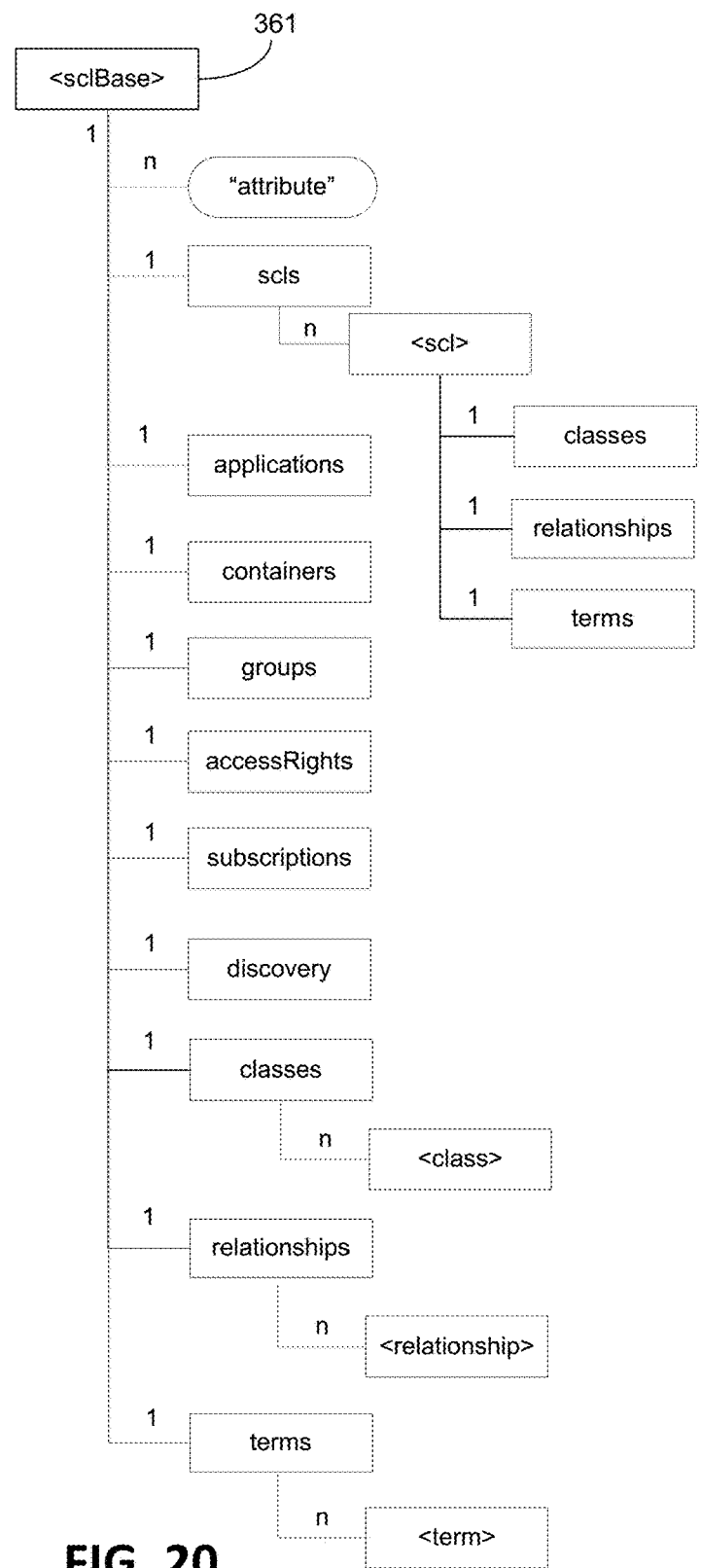
FIG. 20 illustrates a xSCL resource structure.

To support the embodiment of FIG. 19, the xSCL may have the resource structure shown in FIG. 20. The resource collection of the semantics node contains semantics node resources that are created or deleted when a remote SCL having semantics node capability registers or de-registers with the local SCL. Each semantics node resource in this collection may have a corresponding resource structure as shown in FIG. 20. These resources maintain state for remote semantics nodes registered to the local SCL. For example, state such as semantic discovery information (e.g., announced semantic class, representation, and term resources), etc.

The classes, relationships, and terms collections under the <sclBase> resource 361 may each contain respective instances of semantics related resources hosted on the local SCL. Each instance may contain a semantic representation as well as have other attributes associated with it, such as discovery related information such as tags. These collections of semantic related resources may be accessed by clients having the proper access rights to do so.

C. Use Case Example of ETSI M2M Semantics Implementation

The semantics related resources managed by a semantics node may be associated and linked to resources in the ETSI M2M resource structure, such as <sclBase>, <application>, <container>, <contentInstance>, and the like. The following discussion illustrates how semantics related resources may be used to provide semantics information for a <contentInstance>.

Figure 21:
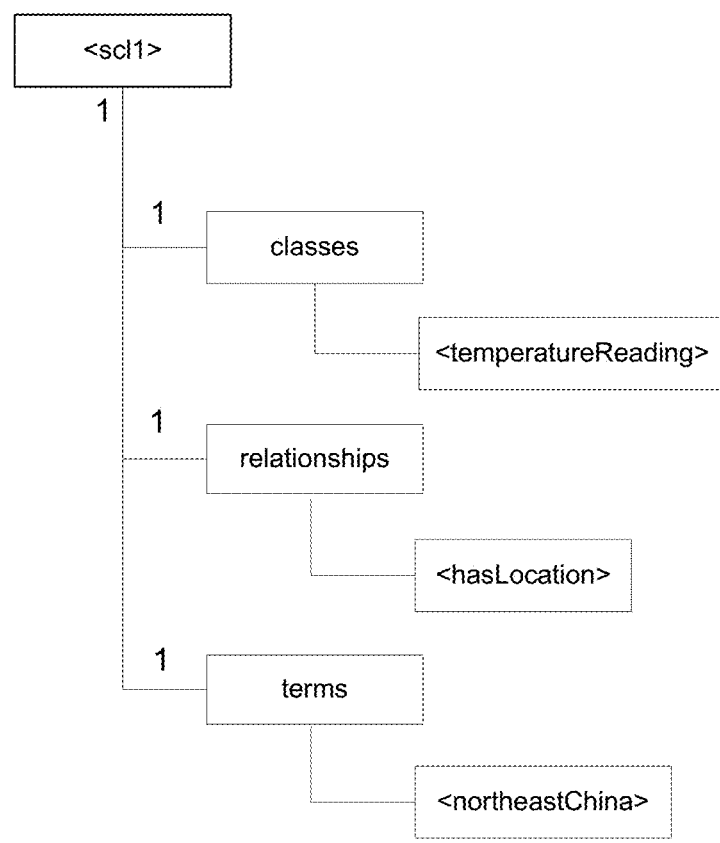
FIG. 21 illustrates a semantics related resource structure on <scl1>.
Figure 22:
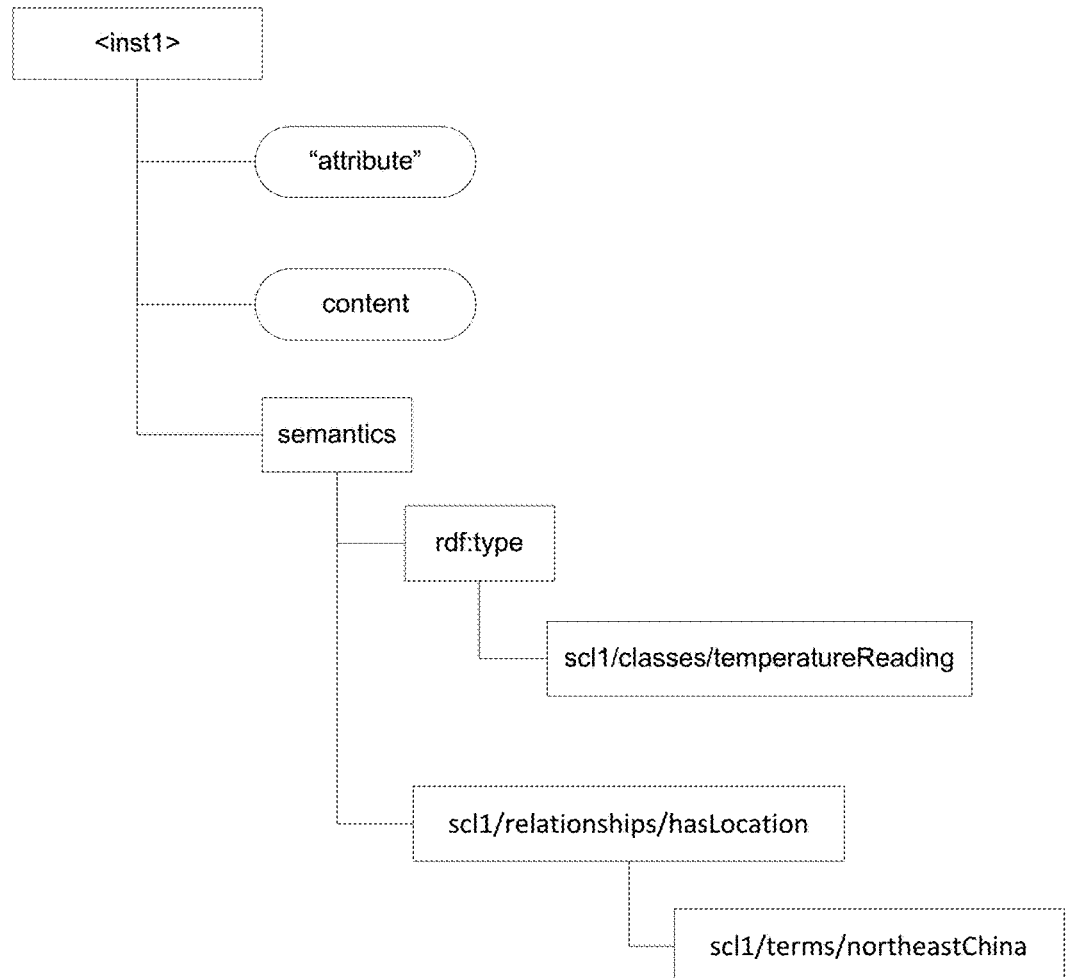
FIG. 22 illustrates a contentInstance semantics.

In this example, assume that a temperatureReading class is defined and stored on scl1, and has URI of scl1/classes/temperatureReading. The relationship hasLocation is defined and stored on scl1 as well, and has URI of scl1/relationships/hasLocation. Additionally, the term 'northeast China' is defined and stored on scl1 too, and has URI of scl1/terms/northeastChina. FIG. 21 shows the semantics related resource structure on <scl1>, which is an example of the xSCL resource structure shown in FIG. 20. This resource structure determines the URIs of the semantics related resources. The contentInstance has a URI of gscl2/applications/app1/containers/<temperature>/contentInstances/<inst1>. By enhancing the contentInstance with the semantics as shown in the xSCL resource structure of FIG. 22, the content of the contentInstance is able to be effectively described and interpreted without ambiguity.

Figure 23:
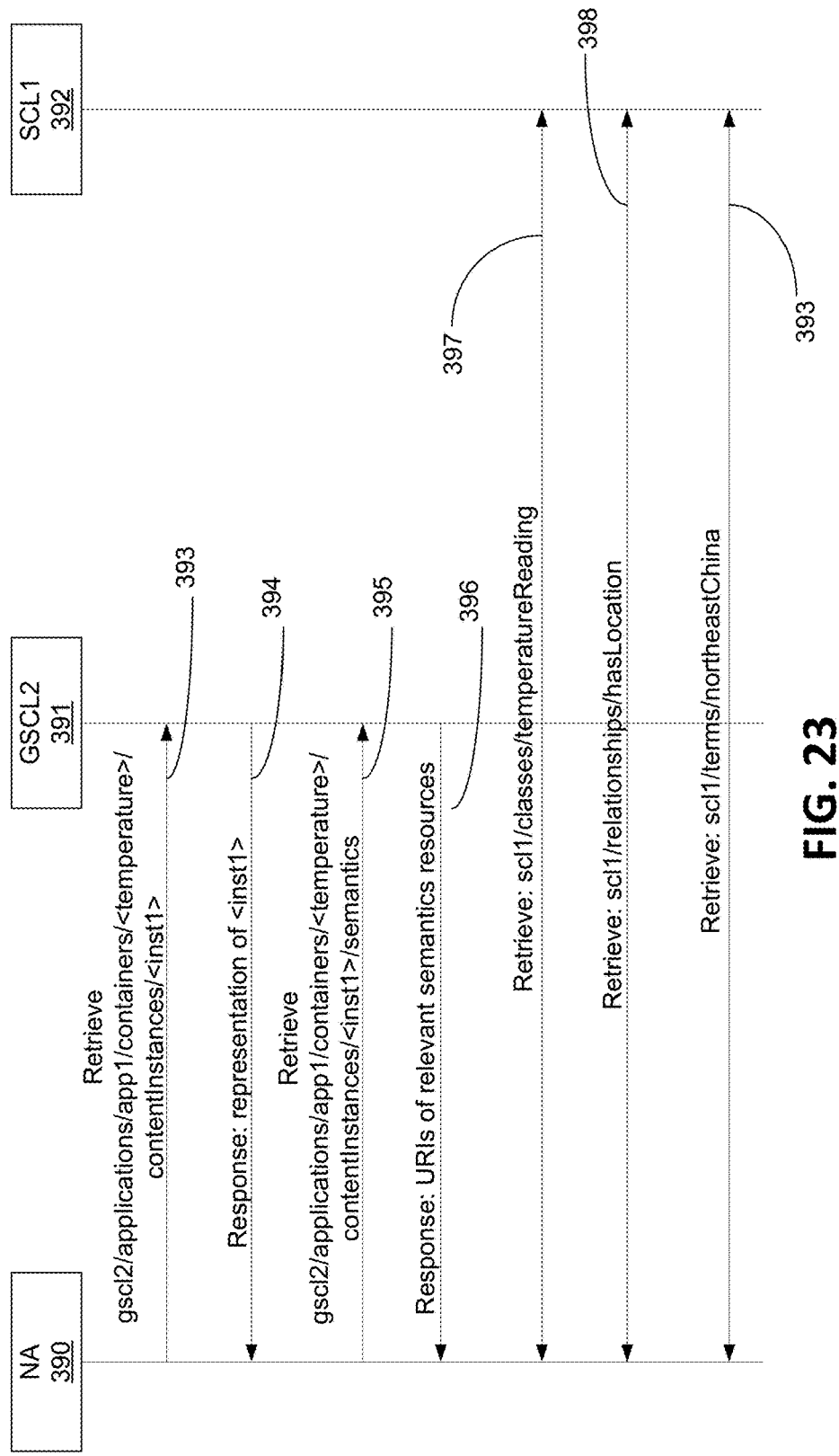
FIG. 23 illustrates a message flow of resource and semantics retrieval.

FIG. 23 is a message flow illustrating one example of resource and semantics retrieval. At step 393, NA 390 sends a RETRIEVE request to GSCL2 391 for a data resource. The data resource, for example, may be a blood pressure sensor reading, core temperature sensor reading, oxygen saturation sensor reading, or motion accelerometer sensor reading, among other things. At step 394, GSCL2 391 returns the representation of the data resource. In order to understand the data resource, the NA needs to retrieve the semantics of the data resource. Accordingly, at step 395, NA 390 sends a retrieve request to the GSCL 391. At step 396, GSCL2 391 returns a list of URIs of the relevant semantics related resources for the data resource, which are stored on SCL1 392. At step 397 through 399, NA 390 exchanges RETRIEVE messages with SCL1 392 for the semantics related resources temperatureReading, hasLocation, and northeastChina, respectively. With these semantics related resources, NA 390 is able to understand the data resources, and therefore can use and manipulate the data resources.

VI. 3GPP MTC Architecture Embodiments

Figure 24:
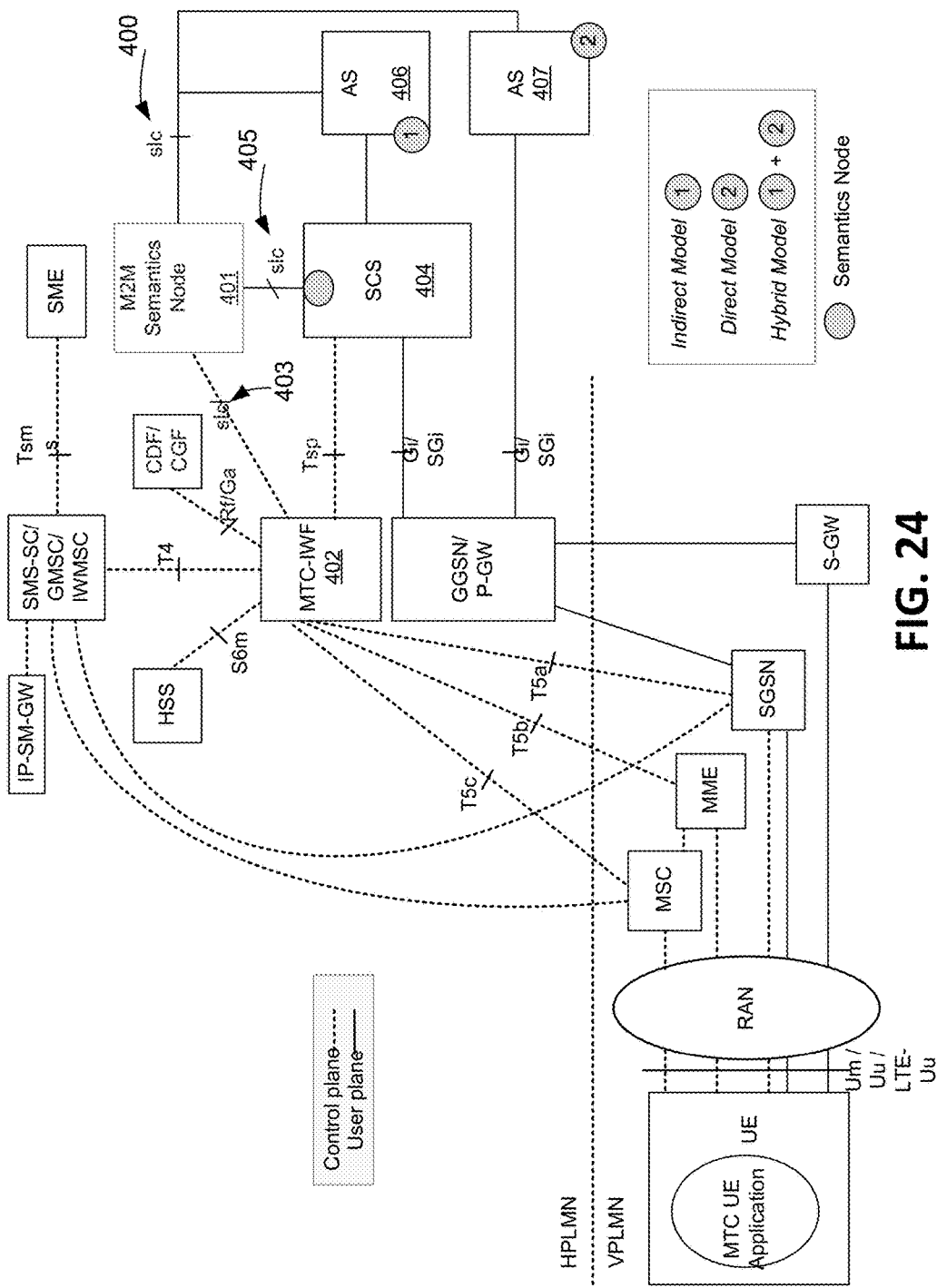
FIG. 24 illustrates a 3GPP MTC architecture with stand-alone semantics nodes.
Figure 25:
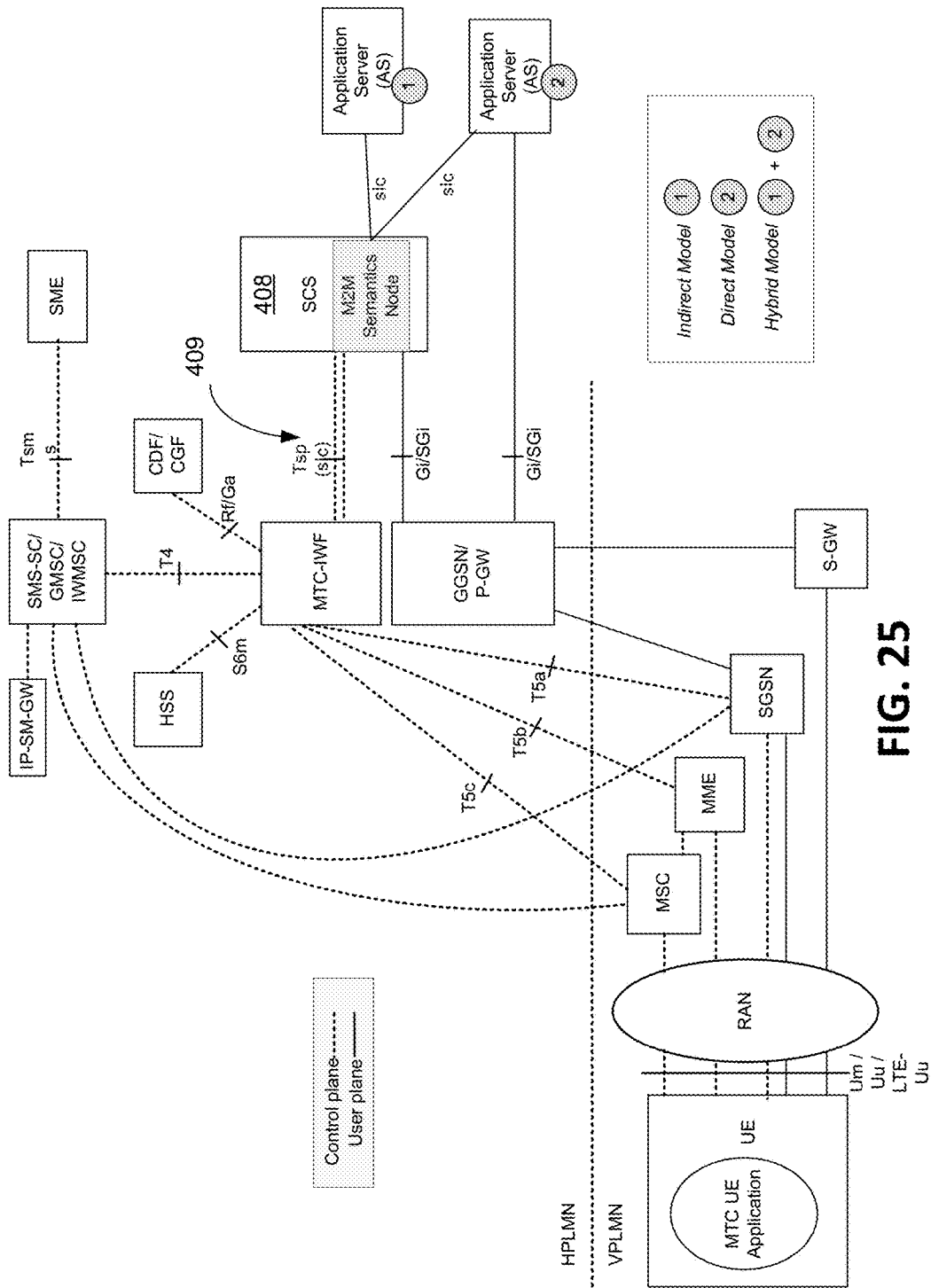
FIG. 25 illustrates a 3GPP MTC architecture with stand-alone semantics nodes.

As further mentioned above, the 3GPP MTC architecture may also be enhanced with the semantics support provided by the semantics nodes described herein. As shown in FIG. 24, in one embodiment, an M2M semantics node 401 may be located outside the 3GPP core network boundary. As further shown, SCS 404 may be enhanced to support a semantics capability and may interface with M2M semantics node 401 via the sIs reference point (not shown). M2M semantics node 401 may also interface with 3GPP machine type communication inter-working function (MTC-IWF) 402 via sIc reference point 403. Application server (AS) 406 and AS 407 may communicate with the M2M semantics node 401 via sIc reference point 400. FIG. 25 illustrates another embodiment for a 3GPP MTC architecture with a semantics node. In this embodiment, the semantic node has been integrated into an SCS 408. As further shown in FIG. 25 at 409, in this embodiment the sIc referent point may be part of 3GPP MTC Tsp.

VII. M2M/IoT Architecture

FIG. 26A through FIG. 26D provide further information concerning an example machine-to machine (M2M) or Internet of Things (IoT) communication system 10 in which one or more disclosed embodiments may be implemented. Generally, M2M technologies provide building blocks for the IoT, and any M2M device, gateway or service platform may be a component of the IoT as well as an IoT service layer, etc.

Figure 26A:
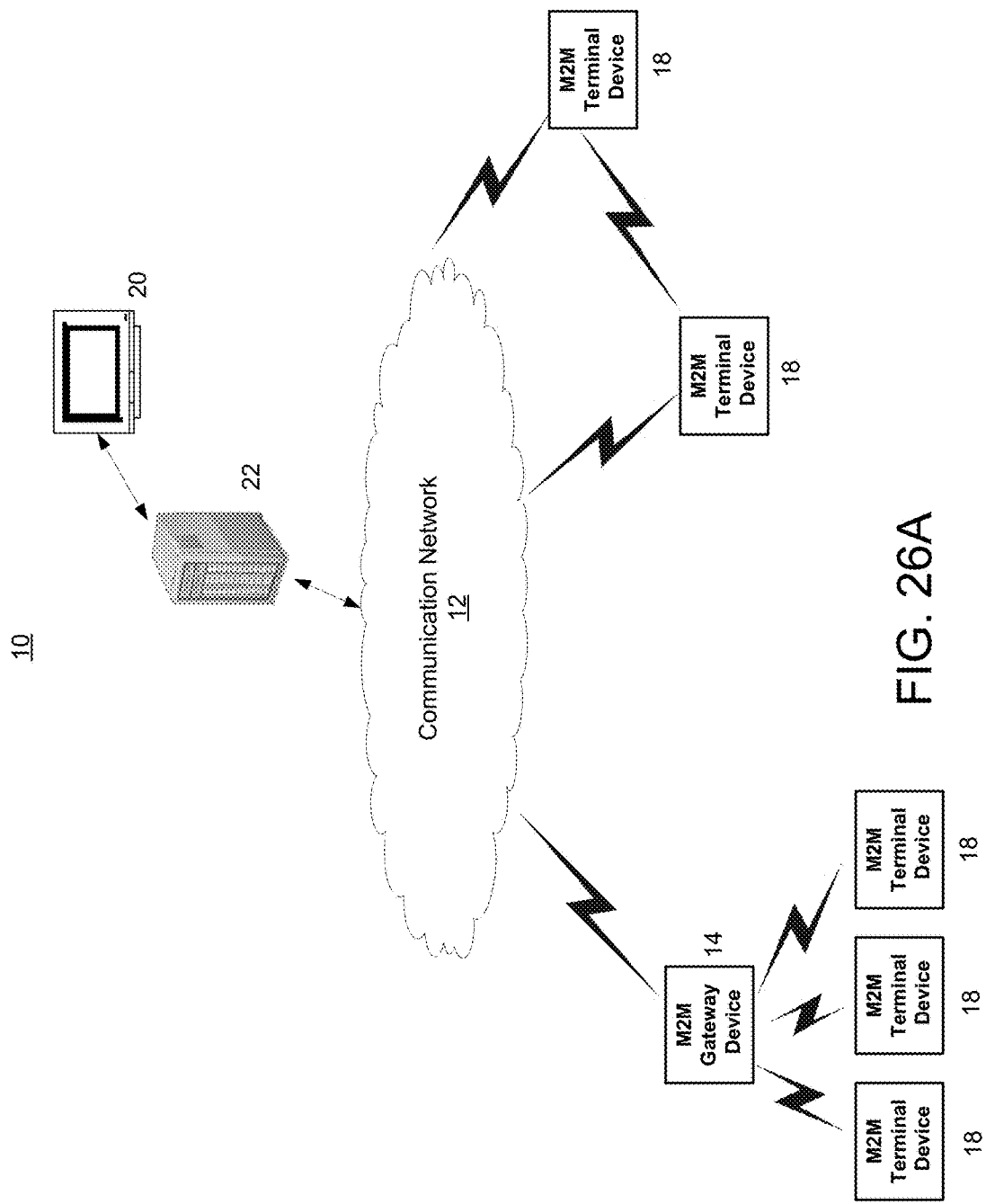
FIG. 26A is a system diagram of an example machine-to-machine (M2M) or Internet of Things (IoT) communication system in which one or more disclosed embodiments may be implemented.

As shown in FIG. 26A, the M2M/IoT communication system 10 includes a communication network 12. The communication network 12 may be a fixed network or a wireless network (e.g., WLAN, cellular, or the like) or a network of heterogeneous networks. For example, the communication network 12 may comprise of multiple access networks that provides content such as voice, data, video, messaging, broadcast, or the like to multiple users. For example, the communication network 12 may employ one or more channel access methods, such as code division multiple access (CDMA), time division multiple access (TDMA), frequency division multiple access (FDMA), orthogonal FDMA (OFDMA), single-carrier FDMA (SC-FDMA), and the like. Further, the communication network 12 may comprise other networks such as a core network, the Internet, a sensor network, an industrial control network, a personal area network, a fused personal network, a satellite network, a home network, or an enterprise network for example.

As shown in FIG. 26A, the M2M/IoT communication system 10 may include an M2M gateway device 14, and M2M terminal devices 18. It will be appreciated that any number of M2M gateway devices 14 and M2M terminal devices 18 may be included in the M2M/IoT communication system 10 as desired. Each of the M2M gateway devices 14 and M2M terminal devices 18 are configured to transmit and receive signals via the communication network 12 or direct radio link. The M2M gateway device 14 allows wireless M2M devices (e.g. cellular and non-cellular) as well as fixed network M2M devices (e.g. PLC) to communicate either through operator networks, such as the communication network 12 or direct radio link. For example, the M2M devices 18 may collect data and send the data, via the communication network 12 or direct radio link, to an M2M application 20 or M2M devices 18. The M2M devices 18 may also receive data from the M2M application 20 or an M2M device 18. Further, data and signals may be sent to and received from the M2M application 20 via an M2M service platform 22, as described below. M2M devices 18 and gateways 14 may communicate via various networks including, cellular, WLAN, WPAN (e.g., Zigbee, 6LoWPAN, Bluetooth), direct radio link, and wireline for example.

The illustrated M2M service platform 22 provides services for the M2M application 20, M2M gateway devices 14, M2M terminal devices 18 and the communication network 12. It will be understood that the M2M service platform 22 may communicate with any number of M2M applications, M2M gateway devices 14, M2M terminal devices 18 and communication networks 12 as desired. The M2M service platform 22 may be implemented by one or more servers, computers, or the like. The M2M service platform 22 provides services such as management and monitoring of M2M terminal devices 18 and M2M gateway devices 14. The M2M service platform 22 may also collect data and convert the data such that it is compatible with different types of M2M applications 20. The functions of the M2M service platform 22 may be implemented in a variety of ways, for example as a web server, in the cellular core network, in the cloud, etc.

Figure 26B:
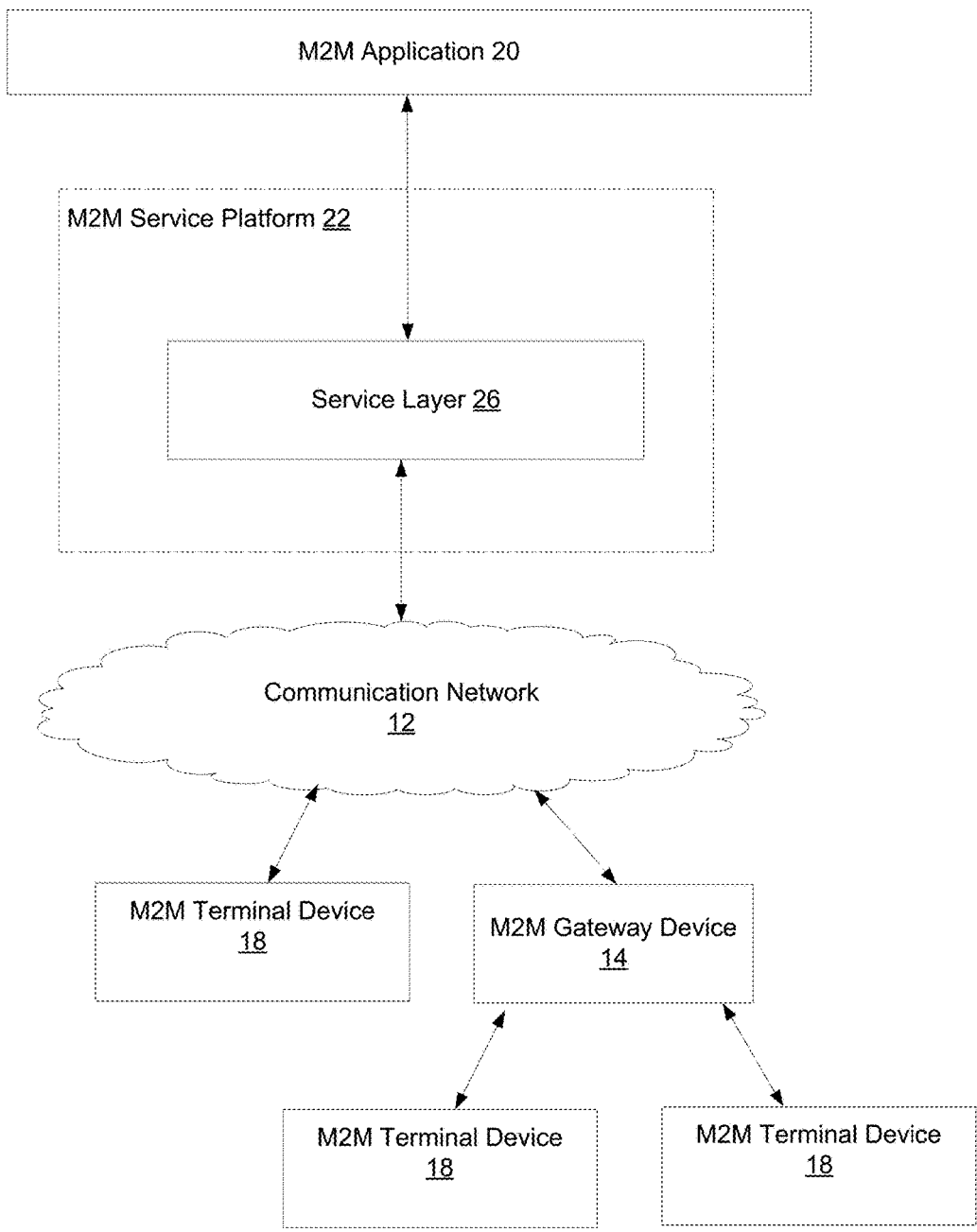
FIG. 26B is a system diagram of an example architecture that may be used within the M2M/IoT communications system illustrated in FIG. 26A.

Referring also to FIG. 26B, the M2M service platform typically implements a service layer 26 (e.g., a D/GSCL) that provides a core set of service delivery capabilities that diverse applications and verticals can leverage. These service capabilities enable M2M applications 20 to interact with devices and perform functions such as data collection, data analysis, device management, security, billing, service/device discovery etc. Essentially, these service capabilities free the applications of the burden of implementing these functionalities, thus simplifying application development and reducing cost and time to market. The service layer 26 also enables M2M applications 20 to communicate through various networks 12 in connection with the services that the service layer 26 provides.

M2M applications 20 may include applications in various industries such as, without limitation, transportation, health and wellness (e.g., patient monitoring application discussed with regard to FIG. 1), connected home, energy management, asset tracking, security, surveillance. As mentioned above, the M2M service layer, running across the devices, gateways, and other servers of the system, supports functions such as, for example, data collection, device management, security, billing, location tracking/geofencing, device/service discovery, and legacy systems integration, and provides these functions as services to the M2M applications 20.

Figure 26C:
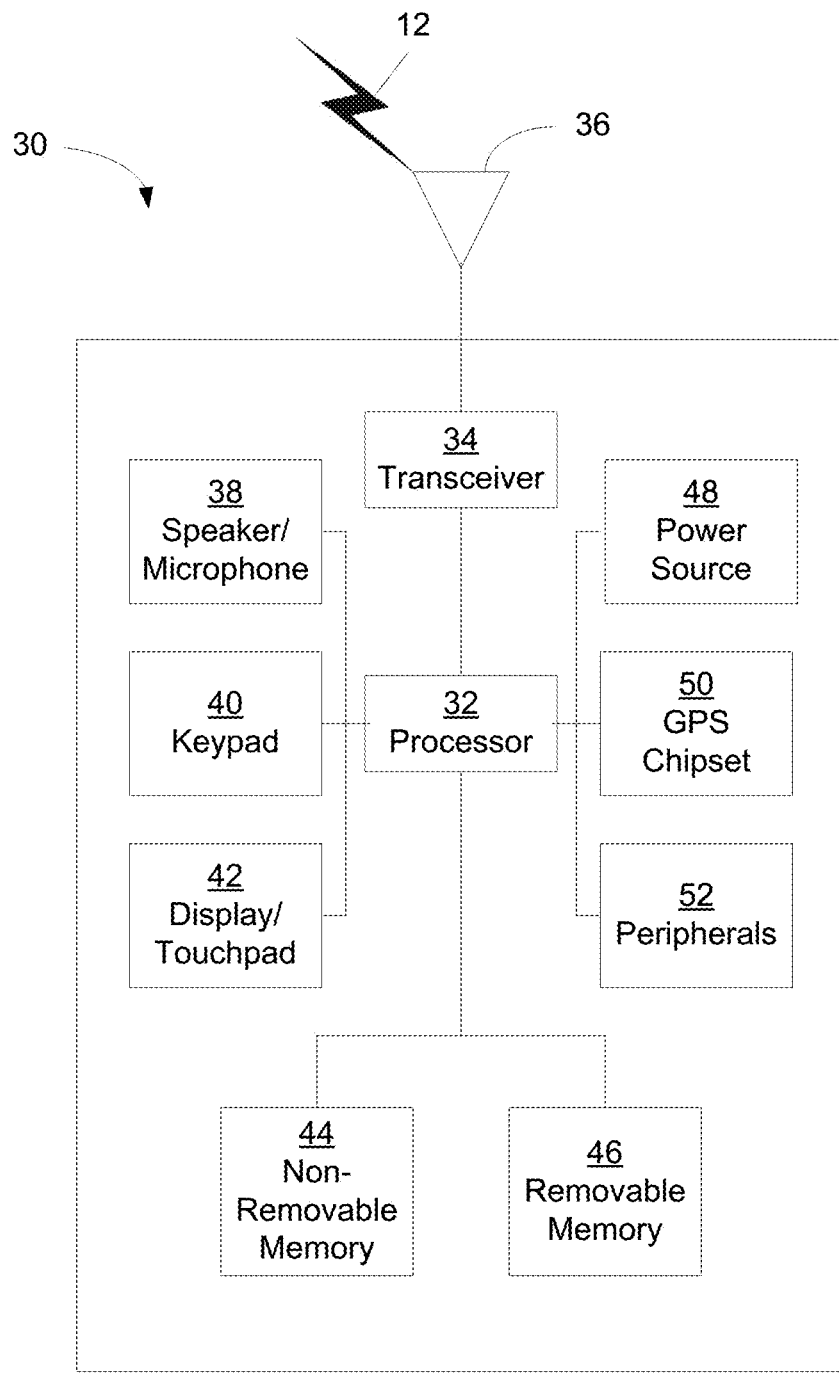
FIG. 26C is a system diagram of an example M2M/IoT terminal or gateway device that may be used within the communications system illustrated in FIG. 26A.

FIG. 26C is a system diagram of an example M2M device 30, such as an M2M terminal device 18 or an M2M gateway device 14 for example. As shown in FIG. 26C, the M2M device 30 may include a processor 32, a transceiver 34, a transmit/receive element 36, a speaker/microphone 38, a keypad 40, a display/touchpad 42, non-removable memory 44, removable memory 46, a power source 48, a global positioning system (GPS) chipset 50, and other peripherals 52. It will be appreciated that the M2M device 30 may include any sub-combination of the foregoing elements while remaining consistent with an embodiment. This device may be a device that uses the disclosed systems and methods for semantics discovery and semantics propagation.

The processor 32 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGAs) circuits, any other type of integrated circuit (IC), a state machine, and the like. The processor 32 may perform signal coding, data processing, power control, input/output processing, and/or any other functionality that enables the M2M device 30 to operate in a wireless environment. The processor 32 may be coupled to the transceiver 34, which may be coupled to the transmit/receive element 36. While FIG. 26C depicts the processor 32 and the transceiver 34 as separate components, it will be appreciated that the processor 32 and the transceiver 34 may be integrated together in an electronic package or chip. The processor 32 may perform application-layer programs (e.g., browsers) and/or radio access-layer (RAN) programs and/or communications. The processor 32 may perform security operations such as authentication, security key agreement, and/or cryptographic operations, such as at the access-layer and/or application layer for example.

The transmit/receive element 36 may be configured to transmit signals to, or receive signals from, an M2M service platform 22. For example, in an embodiment, the transmit/receive element 36 may be an antenna configured to transmit and/or receive RF signals. The transmit/receive element 36 may support various networks and air interfaces, such as WLAN, WPAN, cellular, and the like. In an embodiment, the transmit/receive element 36 may be an emitter/detector configured to transmit and/or receive IR, UV, or visible light signals, for example. In yet another embodiment, the transmit/receive element 36 may be configured to transmit and receive both RF and light signals. It will be appreciated that the transmit/receive element 36 may be configured to transmit and/or receive any combination of wireless or wired signals.

In addition, although the transmit/receive element 36 is depicted in FIG. 26C as a single element, the M2M device 30 may include any number of transmit/receive elements 36. More specifically, the M2M device 30 may employ MIMO technology. Thus, in an embodiment, the M2M device 30 may include two or more transmit/receive elements 36 (e.g., multiple antennas) for transmitting and receiving wireless signals.

The transceiver 34 may be configured to modulate the signals that are to be transmitted by the transmit/receive element 36 and to demodulate the signals that are received by the transmit/receive element 36. As noted above, the M2M device 30 may have multi-mode capabilities. Thus, the transceiver 34 may include multiple transceivers for enabling the M2M device 30 to communicate via multiple RATs, such as UTRA and IEEE 802.11, for example.

The processor 32 may access information from, and store data in, any type of suitable memory, such as the non-removable memory 44 and/or the removable memory 46. The non-removable memory 44 may include random-access memory (RAM), read-only memory (ROM), a hard disk, or any other type of memory storage device. The removable memory 46 may include a subscriber identity module (SIM) card, a memory stick, a secure digital (SD) memory card, and the like. In other embodiments, the processor 32 may access information from, and store data in, memory that is not physically located on the M2M device 30, such as on a server or a home computer. The processor 32 may be configured to control lighting patterns, images, or colors on a display or indicators 42 in response to whether semantics discovery and semantics propogation (e.g., setup or disconnect of a semantics node parent-child relationship) in some of embodiments described herein is successful or unsuccessful, or otherwise indicate the status of resource propagation processes. A user interface viewed via display 42 may give a user an option of subscribing to a semantics node.

The processor 32 may receive power from the power source 48, and may be configured to distribute and/or control the power to the other components in the M2M device 30. The power source 48 may be any suitable device for powering the M2M device 30. For example, the power source 48 may include one or more dry cell batteries (e.g., nickel-cadmium (NiCd), nickel-zinc (NiZn), nickel metal hydride (NiMH), lithium-ion (Li-ion), etc.), solar cells, fuel cells, and the like.

The processor 32 may also be coupled to the GPS chipset 50, which is configured to provide location information (e.g., longitude and latitude) regarding the current location of the M2M device 30. It will be appreciated that the M2M device 30 may acquire location information by way of any suitable location-determination method while remaining consistent with an embodiment.

The processor 32 may further be coupled to other peripherals 52, which may include one or more software and/or hardware modules that provide additional features, functionality and/or wired or wireless connectivity. For example, the peripherals 52 may include an accelerometer, an e-compass, a satellite transceiver, a sensor, a digital camera (for photographs or video), a universal serial bus (USB) port, a vibration device, a television transceiver, a hands free headset, a Bluetooth® module, a frequency modulated (FM) radio unit, a digital music player, a media player, a video game player module, an Internet browser, and the like.

Figure 26D:
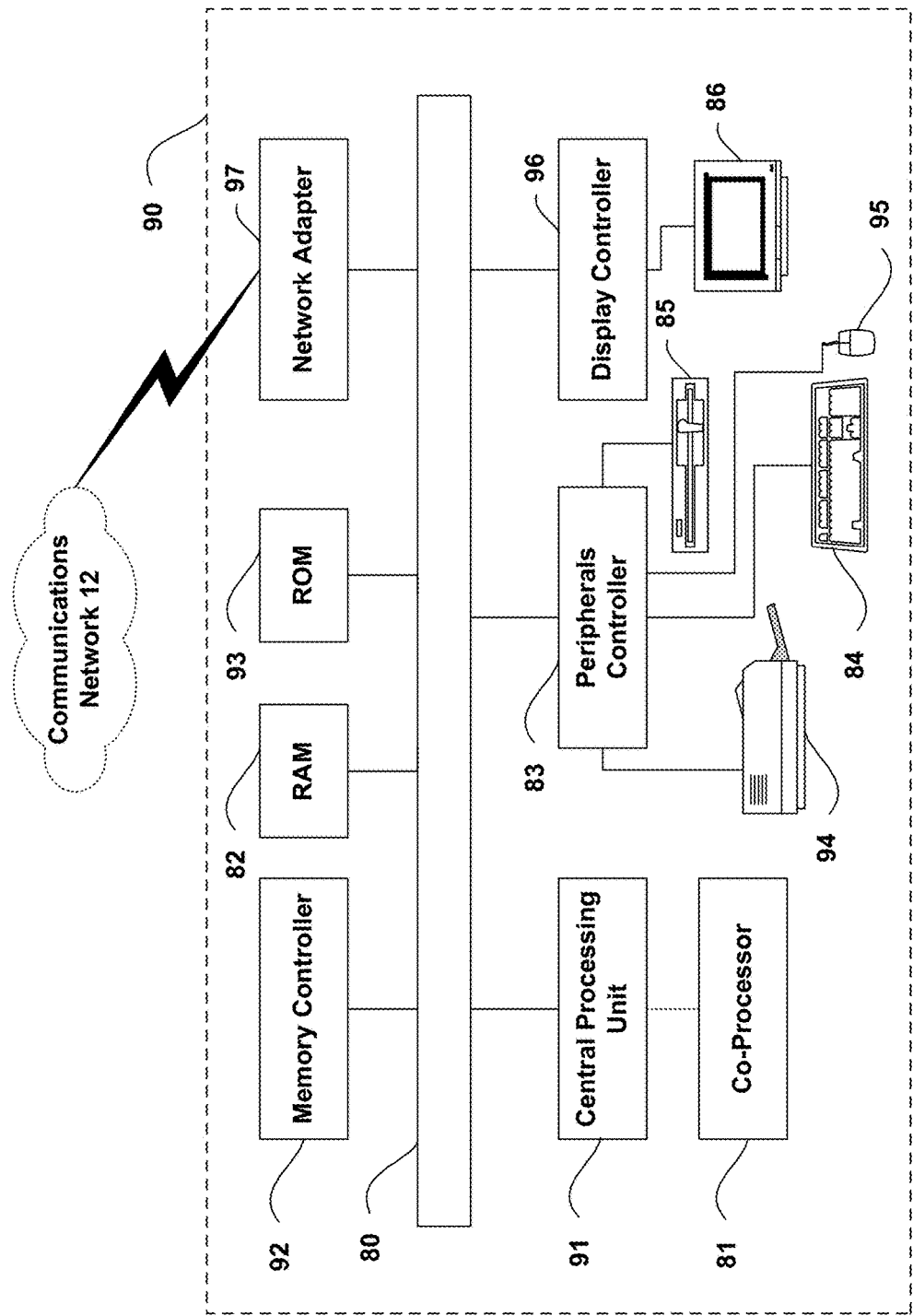
FIG. 26D is a block diagram of an example computing system in which aspects of the communication system of FIG. 26A may be embodied.

FIG. 26D is a block diagram of an exemplary computing system 90 on which, for example, the M2M service platform 22 of FIG. 26A and FIG. 26B may be implemented. Computing system 90 may comprise a computer or server and may be controlled primarily by computer readable instructions, which may be in the form of software, wherever, or by whatever means such software is stored or accessed. Such computer readable instructions may be executed within central processing unit (CPU) 91 to cause computing system 90 to do work. In many known workstations, servers, and personal computers, central processing unit 91 is implemented by a single-chip CPU called a microprocessor. In other machines, the central processing unit 91 may comprise multiple processors. Coprocessor 81 is an optional processor, distinct from main CPU 91, that performs additional functions or assists CPU 91. CPU 91 and/or coprocessor 81 may receive, generate, and process data related to the disclosed systems and methods for semantics support and management, such as receiving semantics related resources from a semantics node.

In operation, CPU 91 fetches, decodes, and executes instructions, and transfers information to and from other resources via the computer's main data-transfer path, system bus 80. Such a system bus connects the components in computing system 90 and defines the medium for data exchange. System bus 80 typically includes data lines for sending data, address lines for sending addresses, and control lines for sending interrupts and for operating the system bus. An example of such a system bus 80 is the PCI (Peripheral Component Interconnect) bus.

Memory devices coupled to system bus 80 include random access memory (RAM) 82 and read only memory (ROM) 93. Such memories include circuitry that allows information to be stored and retrieved. ROMs 93 generally contain stored data that cannot easily be modified. Data stored in RAM 82 can be read or changed by CPU 91 or other hardware devices. Access to RAM 82 and/or ROM 93 may be controlled by memory controller 92. Memory controller 92 may provide an address translation function that translates virtual addresses into physical addresses as instructions are executed. Memory controller 92 may also provide a memory protection function that isolates processes within the system and isolates system processes from user processes. Thus, a program running in a first mode can access only memory mapped by its own process virtual address space; it cannot access memory within another process's virtual address space unless memory sharing between the processes has been set up.

In addition, computing system 90 may contain peripherals controller 83 responsible for communicating instructions from CPU 91 to peripherals, such as printer 94, keyboard 84, mouse 95, and disk drive 85.

Display 86, which is controlled by display controller 96, is used to display visual output generated by computing system 90. Such visual output may include text, graphics, animated graphics, and video. Display 86 may be implemented with a CRT-based video display, an LCD-based flat-panel display, gas plasma-based flat-panel display, or a touch-panel. Display controller 96 includes electronic components required to generate a video signal that is sent to display 86.

Further, computing system 90 may contain network adaptor 97 that may be used to connect computing system 90 to an external communications network, such as network 12 of FIG. 26A and FIG. 26B.

It is understood that any or all of the systems, methods and processes described herein may be embodied in the form of computer executable instructions (i.e., program code) stored on a computer-readable storage medium which instructions, when executed by a machine, such as a computer, server, M2M terminal device, M2M gateway device, or the like, perform and/or implement the systems, methods and processes described herein. Specifically, any of the steps, operations or functions described above may be implemented in the form of such computer executable instructions. Computer readable storage media include both volatile and nonvolatile, removable and non-removable media implemented in any method or technology for storage of information, but such computer readable storage media do not includes signals. Computer readable storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other physical medium which can be used to store the desired information and which can be accessed by a computer.

In describing preferred embodiments of the subject matter of the present disclosure, as illustrated in the Figures, specific terminology is employed for the sake of clarity. The claimed subject matter, however, is not intended to be limited to the specific terminology so selected, and it is to be understood that each specific element includes all technical equivalents that operate in a similar manner to accomplish a similar purpose. For example, although it is illustrated that the target of semantics related resource publishing and discovery are siblings and children, the semantics node can choose other semantics nodes for publishing and discovery that may not have such relationships.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed:

1. A method comprising:
    receiving via a network, by a first computing device, a request from a client device to create a first semantics related resource of a first plurality of semantics related resources on the first computing device, wherein the request comprises a request for a definition associated with a semantics description, wherein the first computing device is a first semantics node;
    determining that the request for the definition associated with the semantics description resides on a second computing device, wherein the second computing device is a second semantics node and the second computing device comprises a second plurality of semantics related resources; and
    responsive to the determining that the request for the definition associated with the semantics description resides on a second computing device, linking the semantics description to the definitions on the second semantics node, wherein the created linking is used for subsequent requests for semantics.

2. The method of claim 1, further comprising:
    sending, by the first computing device, an update of the requested first semantics related resource on the second computing device when the first semantics related resource changes on the first computing device.

3. The method of claim 1, further comprising receiving, by the first computing device, a request to subscribe to receive updates for changes to the first semantics related resource.

4. The method of claim 1, wherein each of the first plurality of semantics related resources comprises one of a class, a relationship, or a term.

5. The method of claim 1, wherein each of the first plurality of semantics related resources has a universal resource identifier.

6. The method of claim 2, wherein the second computing device is a child semantics node.

7. The method of claim 1, further comprising:
receiving a request to move a second semantics related resource of the first plurality of semantics related resources to a third computing device for query by the client device;
forwarding the second semantics related resource to the third computing device; and
subsequent to forwarding the second semantics related resource to the third computing device, deleting the second semantics related resource from the first computing device.

8. The method of claim 7, wherein the request to move the second semantics related resource is based on reaching the threshold of requests for the second semantics related resource.

9. A first semantics node comprising:
a processor;
a transmit/receive element for communicating with a network; and
a memory coupled to the processor, the memory comprising executable instructions that when executed by the processor cause the semantic node to effectuate operations comprising:
receiving, from a client device via the network, a request to create a first semantics related resource of a first plurality of semantics related resources, wherein the request comprises a request for a definition associated with a semantics description;
determining that the request for the definition associated with the semantics description resides on a second semantics node, wherein the second semantics node comprises a second plurality of semantics related resources; and
responsive to the determining that the request for the definition associated with the semantics description resides on a second semantics node, linking the semantics description to the definitions on the second semantics node, wherein the created linking is used for subsequent requests for semantics.

10. The first semantics node of claim 9, wherein the operations further comprise retrieving the requested first semantics related resource from the second semantics node when the first semantics related resource is not included in a plurality of semantics related resources stored in the memory of the first semantics node.

11. The first semantics node of claim 9, wherein the operations further comprise subscribing to receive updates for changes to a second semantics related resource.

12. The first semantics node of claim 10, wherein the second semantics node is a parent semantics node.

13. The first semantics node of claim 9, wherein each of the first plurality of semantics related resources comprises one of a class, a relationship, or a term, and each semantics related resource has a universal resource identifier or a unified resource locator.

14. The first semantics node of claim 9, wherein the operations further comprise:
receiving a request to move a second semantics related resource of the first plurality of semantics related resources to a third semantics node for query by the client device;
forwarding the second semantics related resource to the second semantics node; and
subsequent to forwarding the second semantics related resource to the second semantics node, deleting the second semantics related resource from the memory of the first semantics node.

15. The first semantics node of claim 14, wherein the request to move the second semantics related resource is based on reaching the threshold of requests for the second semantics related resource.

16. A computer readable storage medium comprising computer executable instructions that when executed by a processor of a first computing device cause the computing device to perform operations comprising:
receiving, from a client device via a network, a request from a client device to create a first semantics related resource of a first plurality of semantics related resources on the first computing device, wherein the request comprises a request for a definition associated with a semantics description, wherein the first computing device is a first semantics node;
determining that the request for the definition associated with the semantics description resides on a second computing device, wherein the second computing device is a second semantics node and the second computing device comprises a second plurality of semantics related resources; and
responsive to the determining that the request for the definition associated with the semantics description resides on a second computing device, linking the semantics description to the definitions on the second semantics node, wherein the created linking is used for subsequent requests for semantics.

17. The computer readable storage medium of claim 16, wherein the operations further comprise retrieving the requested first semantics related resource from the second computing device when the first semantics related resource is not included in the first plurality of semantics related resources stored on the first computing device.

18. The computer readable storage medium of claim 16, wherein each semantics related resource comprises one of a class, a relationship, or a term and each semantics related resource has a unified resource locator.

19. The computer readable storage medium of claim 16, wherein the operations further comprise subscribing to receive updates for changes to a second semantics related resource.

* * * * *